(12) United States Patent
Ranki et al.

(10) Patent No.: US 7,803,532 B2
(45) Date of Patent: Sep. 28, 2010

(54) METHOD FOR THE DIAGNOSIS OF LYMPHOPROLIFERATIVE DISEASES

(75) Inventors: Annamari Ranki, Helsinki (FI); Leena Karenko, Helsinki (FI); Marketta Kähkönen, Tampere (FI); Ritva Karhu, Tampere (FI); Tapio Visakorpi, Tampere (FI); Boguslaw Nedoszytko, Gdansk (PL)

(73) Assignee: Helsingin Yliopiston Rahastot, Helsinki (FI)

( * ) Notice: Subject to any disclaimer, the term of this patent is extended or adjusted under 35 U.S.C. 154(b) by 347 days.

(21) Appl. No.: 10/502,638

(22) PCT Filed: Jan. 24, 2003

(86) PCT No.: PCT/FI03/00061

§ 371 (c)(1),
(2), (4) Date: Aug. 24, 2004

(87) PCT Pub. No.: WO03/066898

PCT Pub. Date: Aug. 14, 2003

(65) Prior Publication Data

US 2005/0221309 A1  Oct. 6, 2005

(30) Foreign Application Priority Data

Jan. 24, 2002  (FI) .................................. 20020132
Sep. 10, 2002  (FI) .................................. 20021617

(51) Int. Cl.
*C12Q 1/68* (2006.01)
*C12P 19/34* (2006.01)
*C07H 21/02* (2006.01)
*C07H 21/04* (2006.01)

(52) U.S. Cl. .......................... 435/6; 435/91.2; 536/23.1; 536/23.5

(58) Field of Classification Search ........................ None
See application file for complete search history.

(56) References Cited

U.S. PATENT DOCUMENTS 6,007,994 A * 12/1999 Ward et al. ..................... 435/6

OTHER PUBLICATIONS

Strausberg et al. NCBI Database, National Center for Biotechnology Information, NIH (Bethesda, MD, USA), GenBank Accession No. BC017667, Dec. 6, 2001.*
Strausberg et al. NCBI Database, National Center for Biotechnology Information, NIH (Bethesda, MD, USA), GenBank Accession No. BC017667, Sep. 30, 2003.*
Coy et al. Gene. 2002. 290: 73-94.*
Maes et al. Genomics. Jul. 2002. 80: 21-30.*
Vermeer et al. Cancer Research. Apr. 2008. 68(8) Supplemental Table 4.*

Ayton et al. "Molecular mechanisms of leukemogenesis mediated by MLL fusion proteins" Oncogene 20:5695-5707 (2001).
Beylot-Barry et al. "Characterization of t(2;5) reciprocal transcripts and genomic breakpoints in CD30+ cutaneous lymphoproliferations" Blood 91:4668-4676 (1998).
Cuneo et al. "A novel recurrent translocation t(11;14)(p11;q32) in splenic marginal zone B cell lymphoma" Leukemia 15:1262-1267 (2001).
Fukuhara et al. "Chromosome abnormalities in poorly differentiated lymphocytic lymphoma" Cancer Res. 39:3119-3128 (1979).
Guitart et al. "A new polymerase chain reaction-based method for the detection of T-cell clonality in patients with possible cutaneous T-cell lymphoma" Arch Dermatol. 135:158-162 (1999).
Henegariu et al. "Colour-changing karyotyping: An alternative to M-FISH/SKY" Nature Gen. 23:263-264 (1999).
Hjalgrim et al. "Recent increase in the incidence of non-Hodgkin's lymphoma among young men and women in Denmark" Bri. J. of Cancer 73:951-954 (1996).
Johnstone et al. "Mapping of the human PAWR (par-4) gene to chromosome 12q21" Genomics 53:241-243 (1998).
Kadin et al. "The t(2;5) in human lymphomas" Leukemia and Lymphoma 29:249-256 (1998).
Karendo et al. Chromosomally clonal T Cells in the skin, blood, or lymph nodes of two sezary syndrome patients express CD45RA, CD45RO, CDw150, and interleukin-4, but not interleukin-2 or interferon-γ J. Invest. Dermatol. 116:188-193 (2001).
Karenko et al. "Notable losses at specific regions of chromosomes 10q and 13q in the sézary syndrome detected by comparative genomic hybridization" J. Invest. Dermatol. 112:392-395 (1999).
Karenko et al. "Chromosomal abnormalities in cutaneous T-cell lymphoma and its premalignant conditions as detected by G-banding and interphase cytogenetic methods" J. Invest. Dermatol. 108:22-29 (1997).
Karenko et al. "Clinical and laboratory investigations chromosomal abnormalities in relation to clinical disease in patients with cutaneous T-cell lymphoma: A 5-year follow-up study" Bri. J. Dermatol. 148:55-64 (2003).

(Continued)

*Primary Examiner*—Carla Myers
(74) *Attorney, Agent, or Firm*—Nixon & Vanderhye P.C.

(57) ABSTRACT

The present invention relates to novel methods for the diagnosis and therapy of lymphoproliferative diseases. Specifically, the present invention relates to novel methods for the diagnosis and therapy taking advantage of the detection of chromosomal breakpoints in chromosome 12 and/or translocation of chromosomal material from chromosome 12, said chromosomal breakpoints and/or translocation(s) being associated with lymphoproliferative diseases, such as primary cutaneous T-cell lymphomas (CTCL). The present invention further relates to the use of neuron navigator 3 gene (NAV3) or an equivalent or functional fragment thereof involved in chromosomal breakpoints in chromosome 12 and/or translocations thereof, said gene and/or translocations thereof being associated with lymphoproliferative diseases, such as primary cutaneous T-cell lymphomas (CTCL), as a diagnostic and therapeutic agent. The present invention also relates to the development of therapy.

6 Claims, 9 Drawing Sheets

OTHER PUBLICATIONS

Kazmierczak et al. "Description of a novel fusion transcript between HMGI-C, a gene encoding for a member of the high mobility group proteins, and the mitochondrial aldehyde dehydrogenase gene" Cancer Res. 55:6038-6039 (1995).

Muche et al. "Cellular coincidence of clonal T cell receptor rearrangements and complex clonal chromosomal aberrations—a hallmark of malignancy in cutaneous T cell lymphoma" J. Invest. Dermatol. 122:574-578 (2004).

Muzny et al. "*Homo sapiens* 12 BAC RP11-359M6" NCBI Accession No. AC027288 (2002).

Nowell et al. "A minute chromosome in human chronic granulocytic leukemia" Science 142:1497 (1960).

Rogalla et al. "Significant correlation between the breakpoints of rare clonal aberrations in benign solid tumors and the assignment of HMGIY retropseudogenes" Cancer Genet. Cytogen. 130:51-56 (2001).

Schoenmakers et al. "Recurrent rearrangements in the high mobility group protein gene, HMGI-C, in benign mesenchymal tumours" Nature Genet. 10:436-444 (1995).

Schoenmakers et al. "A 6-Mb yeast artificial chromosome contig and long-range physical map encompassing the region on chromosome 12q15 frequently rearranged in a variety of benign solid tumors" Genomics 29:665-678 (1995).

Schröck et al. "Multicolor spectral karyotyping of human chromosomes" Science 273:494-497 (1996).

Shtivelman et al. "Fused transcript of *abl* and *bcr* genes in chronic myelogenous leukaemia" Nature 315:550-554 (1985).

Siegel et al. "Primary cutaneous T-cell lymphoma: Review and current concepts" J. Clin. Oncol. 18:2908-2925 (2000).

Speicher et al. "Karyotyping human chromosomes by combinatorial multi-fluor FISH" Nature Genet. 12:368-375 (1996).

Stringham et al. "*unc*-53 controls longitudinal migration in *C. elegans*" Development 129:3367-3379 (2002).

Tanke et al. "New strategy for multi-colour fluorescence in situ hybridisation: COBRA: Combined binary ratio labelling" Eur. J. Human Gen. 7:2-11 (1999).

Väkevä et al. "Increased risk of secondary cancers in patients with primary cutaneous T cell lymphoma" J. Invest. Dermatol. 115:62-65 (2000).

Veelken et al. "Molecular staging of cutaneous T-cell lymphoma: Evidence for systemic involvement in early disease" J. Invest. Dermatol. 104:889-894 (1995).

Whang-Peng et al. "Clinical implications of cytogenetic studies in cutaneous T-cell lymphoma (CTCL)" Cancer 50:1539-1553 (1982).

Willemze et al. "EORTC classification for primary cutaneous lymphomas: A proposal from the cutaneous lymphoma study group of the European Organization for Research and Treatment of Cancer" Blood 90:354-371 (1997).

Wolfe et al. "Large-cell transformation following detection of minimal residual disease in cutaneous T-cell lymphoma: Molecular and in situ analysis of a single neoplastic T-cell clone expressing eh identical T-cell receptor" J. Clin. Oncol. 13:1751-1757 (1995).

Xu et al. "Molecular cytogenetic characterization and clinical relevance of additional, complex and/or variant chromosome abnormalities in acute promyelocytic leukemia" Leukemia 15:1359-1368 (2001).

Zackheim "Cutaneous T Cell lymphoma: Update of treatment" Dermatol. 199:102-105 (1999).

Karenko et al. "Primary cutaneous T-cell lymphomas show a deletion or translocation affecting NAV3, the human UNC-53 homologue" Cancer Res. 65:8101-8110 (2005).

Karku et al. "Chromosome arm-specific multicolor fish" Genes, Chromosomes & Cancer 30:105-109 (2001).

Marty et al. "Primary cutaneous T-cell lymphomas do not show specific NAV3 gene deletion or translocation" J. Invest. Dermatol. Advanced Online Publication pp. 1-9 (2008).

Olsen et al. "Revisions to the staging and classification of mycosis fungoides and Sezary syndrome: A proposal of the International Society for Cutaneous Lymphomas (ISCL) and the cutaneous lymphoma task force of the European Organization of Research and Treatment of Cancer (EORTC)" Blood 110:1713-1722 (Sep. 2007).

Vermeer et al. "Novel and highly recurrent chromosomal alterations in Sézary syndrome" Cancer Res. 68:2689-2698 (Apr. 2008).

Willemze et al. "WHO-EORTC classification for cutaneous lymphomas" Blood 105:3768-3785 (May 2005).

* cited by examiner

SEQUENCE LISTING

<160> NUMBER OF SEQ ID NOS: 3

<210> SEQ ID NO 1
<211> LENGTH: 6849
<212> TYPE: DNA
<213> ORGANISM: Homo sapiens

<400> SEQUENCE: 1

```
atttacactg actgggccaa ccactaccta gcaaaatcag gccacaagcg gctgatcaag      60
gacttgcaac aagacattgc agatggagta ctcctggcag aaatcatcca gattattgca     120
aatgaaaaag ttgaagatat caatggatgt cctagaagtc agtctcagat gattgaaaat     180
gttgatgtct gccttagttt tctagcagcc agaggggtaa atgttcaagg tctatctgct     240
gaagaaataa gaaatggaaa cttaaaagcc attctagggc tgttttttcag tttatctcgc    300
tacaagcagc aacaacacca tcaacaacag tactatcagt ccttggtgga acttcagcag    360
cgagttactc acgcttcccc tccatcggaa gccagccagg ccaaaaccca gcaagatatg    420
cagtccagtc tggcagccag atatgcaact cagtctaatc acagtggaat tgcaaccagt    480
caaaaaaagc ctactaggct tccagggccc tctagggtgc ctgctgcagg aagcagcagc    540
aaggtccagg gagcctctaa tttaaatagg agaagtcaga gctttaacag cattgacaaa    600
aacaagcctc caaattatgc aaatggaaac gaaaaagatt cctccaaagg acctcaatcg    660
tcttcaggtg taaatggtaa cgtgcagcct cccagtactg ctgggcagcc tcctgcctct    720
gccatccctt ctccaagtgc cagcaagccc tggcgcagca agtccatgaa tgtcaaacac    780
agtgccacct ccaccatgtt gactgtaaag cagtcaagta cagccaccta ccccacacca    840
tcttcagaca gactgaagcc acctgtctca gaaggggtca aaactgctcc ctcaggacag    900
aaatccatgc ttgagaaatt caagctagtc aatgcccgga ctgctttacg ccccccgcag    960
cctcccagtt caggacctag tgatggtggg aaggatgatg atgccttttc tgaatctggt   1020
gaaatggaag ttttaacag tggtctgaat agtggtggct caacaaatag cagtcccaaa   1080
gtgtcaccta agttggcccc tccaaaagct ggaagcaaaa atctcagcaa taaaaagtct   1140
ttgctacagc caaggaaaa agaagaaaag aacagggaca aaaataaagt ttgcactgaa   1200
aaaccagtca agaagagaa ggatcaggtg acagagatgg ctccaaaaaa gacctccaaa   1260
attgcaagct tgatccctaa gggcagcaag acaacagcag ctaagaagga aagcttaatt   1320
ccgtcttcca gtggtattcc aaaaaccagc tctaaagttc aacagtaaa gcaaaccatt   1380
tcacctggca gcacagcaag caaagagtct gagaaattca ggactaccaa ggggagccct   1440
tcccagtcct tatctaagcc tataaccatg gagaaagcaa gtgcttctag ttgtcctgcc   1500
cctttggaag gagggaagc tggccaagct tctccttctg gttcctgtac catgacagtg   1560
gcacaaagca gtgggcagag cacaggaaat ggtgctgtcc aactccctca acagcagcaa   1620
catagccacc gaataccgc gacagtggca ccattcattt acagggcaca ttcagaaaat   1680
gaaggtaccg ctttaccatc ggctgactcc tgtaccagtc ctacaaagat ggacttatca   1740
tatagtaaga ctgctaagca gtgcctggag gagatatctg gtgaagaccc tgaaacaaga   1800
agaatgagaa cagttaaaaa catagcagac ttgaggcaga atttagaaga gactatgtcc   1860
agtcttcgtg ggactcagat aagccacagc accctggaga caacatttga cagcactgtg   1920
acaacagaag ttaatggaag gaccataccc aacttgacaa gtcgacccac ccccatgacc   1980
tggaggttgg gccaggcatg tccgcgactt caggcgggag atgctccctc cctgggtgct   2040
```

```
ggctatcctc gcagtggtac cagtcgattc atccacacag acccctcgag gttcatgtat   2100
accacgcctc tccgtcgagc tgctgtctct aggctgggaa acatgtcaca gattgacatg   2160
agtgagaaag caagcagtga cctggacatg tcttctgagg tcgatgtggg tggatatatg   2220
agtgatggtg atatccttgg gaaaagtctc aggactgatg acatcaacag tgggtacatg   2280
acagatggag gacttaacct atatactaga agtctgaacc gaataccaga cacagcaact   2340
tcccgggaca tcatccagag aggggttcac gatgtgacag tggatgcaga cagctgggat   2400
gacagcagtt cagtgagcag tggtctcagt gacacccttg ataacatcag cactgatgac   2460
ctgaacacca catcctctgt cagctcttac tccaacatca ccgtcccctc taggaagaat   2520
actcaggtga ggacagattc agagaaacgc tccaccacag acgagacctg ggatagtcct   2580
gaggaactga aaaaccaga agaagatttt gacagccatg gggatgctgg tggcaagtgg   2640
aagactgtgt cctctggact tcctgaagac cccgagaagg cagggcagaa agcttccctg   2700
tctgtttcac agacaggttc ctggagaaga ggcatgtctg cccaaggagg ggcgccatct   2760
aggcagaaag ctggaacaag tgcactcaaa acacccggga aaaccgatga tgccaaagct   2820
tctgagaaag gaaaagctcc cctaaaagga tcatctctac aaagatctcc ttcagatgca   2880
ggaaaaagca gtgagatgga agggaaaaag ccccccctcag gcattggaag atcgactgcc   2940
accagctcct ttggctttaa gaaaccaagt ggagtagggt catctgccat gatcaccagc   3000
agtggagcaa ccataacaag tggctctgca acactgggta aaattccaaa atctgctgcc   3060
attggcggga agtcaaatgc agggagaaaa accagtttgg acggttcaca gaatcaggat   3120
gatgttgtgc tgcatgttag ctcaaagact accctacaat atcgcagctt gccccgccct   3180
tcaaaatcca gcaccagtgg cattcctggc cgaggaggcc acagatccag taccagcagt   3240
attgattcca acgtcagcag caagtctgct ggggccacca cctcgaaact gagagaacca   3300
actaaaattg ggtcagggcg ctcgagtcct gtcaccgtca accaaacaga caaggaaaag   3360
gaaaaagtag cagtctcaga ttcagaaagt gtttctttgt caggttcccc caaatccagc   3420
cccacctctg ccagcgcctg tggtgcacaa ggtctcaggc agccaggatc caagtatcca   3480
gatattgcct cacccacatt tcgaaggttg tttggtgcca aggcaggtgg caaatctgcc   3540
tctgcaccta atactgaggg tgtgaaatct tcctcagtaa tgcccagccc tagtaccaca   3600
ttagcgcggc aaggcagtct ggagtcaccg tcgtccggta cgggcagcat gggcagtgct   3660
ggtgggctaa gcggcagcag cagccctctc ttcaataaac cctcagactt aactacagat   3720
gttataagct taagtcactc gttggcctcc agcccagcat cggttcactc tttcacatca   3780
ggtggtctcg tgtgggctgc caatatgagc agttcctctg caggcagcaa ggatactccg   3840
agctaccagt ccatgactag cctccacacg agctctgagt ccattgacct cccctcagc    3900
catcatggct ccttgtctgg actgaccaca ggcactcacg aggtccagag cctgctcatg   3960
agaacgggta gtgtgagatc tactctctca gaaagcatgc agcttgacag aaatacacta   4020
cccaaaaagg gactaagata tacccccatca tctcggcagg ccaaccaaga agagggcaaa   4080
gagtggttgc gttctcattc tactggaggg cttcaggaca ctggcaacca gtcacctctg   4140
gtttccccctt ctgccatgtc atcttctgca gctggaaaat accactttc taacttggtg   4200
agcccaacaa atttgtctca gtttaacctt cccgggccca gcatgatgcg ctcaaacagc   4260
atcccagccc aagactcttc cttcgatctc tatgatgact cccagctttg tgggagtgcc   4320
acttctctgg aggaaagacc tcgtgccatc agtcattcgg gctcattcag agacagcatg   4380
```

```
gaagaagttc atggctcttc attatcactg gtgtccagca cttcttctct ttactctaca   4440
gctgaagaaa aggctcattc agagcaaatc cataaactgc ggagagagct ggttgcatca   4500
caagaaaaag ttgctaccct cacatctcag ctttcagcaa atgctcacct tgtagcagct   4560
tttgaaaaga gcttagggaa tatgactggc cgattgcaaa gtctaactat gacagcggaa   4620
caaaaggaat ctgaacttat agaactaaga gaaaccattg aaatgctgaa ggctcagaat   4680
tctgctgccc aggcggctat tcagggagca ctgaatggtc cagaccatcc tcccaaagat   4740
cttcgcatca gaagacagca ttcctctgaa agtgtttcta gtatcaacag tgccacaagc   4800
cattccagta ttggcagtgg taatgatgcc gactccaaga agaagaaaaa gaaaaactgg   4860
gtgaactcta gaggaagtga gctgagaagt tctttcaaac aagcctttgg gaagaaaaag   4920
tccaccaagc ctccttcatc acattctgac attgaagagc ttactgattc atcccttccg   4980
gcatccccca gttaccccca taatgctggt gactgtggct cagcatccat gaagccctca   5040
caatctgctt cagcgatctg tgaatgcaca gaagctgagg cagagataat tctgcagctg   5100
aagagcgagc tcagagaaaa ggaattaaaa ttaacggata ttcggctgga ggccctcagc   5160
tctgctcatc atcttgatca gatccgggaa gccatgaacc ggatgcagaa tgaaattgaa   5220
atactgaaag ctgaaaatga ccggttgaag gcagaaactg gtaacacagc taagcctact   5280
cggccaccgt cagaatcctc aagcagcacc tcctcttcat cttccaggca gtcattagga   5340
cttttctctaa acaatttgaa catcacagag gctgttagct cagatatttt gctagatgat   5400
gctggtgatg caactggaca taaagatggc cgcagtgtga aaattatagt ctccataagc   5460
aagggctatg gtcgagcaaa ggaccaaaaa tctcaggcat atttgatagg atccattggt   5520
gttagtggaa aaaccaagtg ggatgtctta gatggtgtaa taagacgtct ctttaaggaa   5580
tatgtattcc gaattgatac atccactagc cttggtctga gctctgactg cattgctagc   5640
tactgtatag gagacttaat tagatcccat aacctagaag tgcctgaatt gctgccttgt   5700
ggataccttg ttggagataa taacatcatc actgtgaacc tcaaaggggt agaagaaaat   5760
agtttggaca gttttgtttt tgatacgctg attcctaaac caattaccca aaggtacttt   5820
aacttgttga tggagcatca cagaattata ctctcaggac cgagtggtac tggaaagacc   5880
tatttggcaa acaaacttgc tgaatatgta ataaccaaat ctggaaggaa aaaaacagag   5940
gatgcaattg ccacttttaa tgtggaccac aagtcaagta aggaattgca acaatatcta   6000
gctaacctgg ctgaacagtg cagtgctgat aataatggag tggagctccc agttgtaata   6060
attcttgata atcttcatca tgtgggctct ctgagtgata tcttcaatgg ttttctcaat   6120
tgtaaataca caaatgtcc atatattatt ggaacaatga atcagggagt tcttcatca   6180
ccaaatctag agctgcatca caatttcagg tgggtattat gtgcaaatca tacagaacca   6240
gtgaaaggct ttttaggcag atatcttcga agaaaactca tagagataga aattgaaagg   6300
aacattcgca ataatgacct agtcaaaatt atagattgga ttccgaagac gtggcatcat   6360
ctcaacagtt ttttggaaac acacagttct tctgacgtta ccattggtcc ccgactattc   6420
cttccttgcc ccatggatgt agaaggttct agagtatggt tcatggatct ctggaactat   6480
tcttttagtac cttatattct ggaggcagtg agagagggtc ttcagatgta tgggaaacgc   6540
acaccatggg aagatccttc aaagtgggtg cttgacacat atccatggag ctcagcaact   6600
ctgcctcagg agagcccagc cttacttcag ctgcgaccag aagatgttgg gtatgaaagc   6660
tgcacatcca ctaaggaagc cacaacctca agcacattc cacaaactga cacagaagga   6720
gatcccctga tgaatatgct aatgaaactc caagaagcag ccaattactc gagcacacaa   6780
```

```
agctgcgaca gcgaaagcac cagccaccat gaagacattt tggattcatc tcttgaatct    6840
accctctga                                                            6849

<210> SEQ ID NO 2
<211> LENGTH: 794
<212> TYPE: DNA
<213> ORGANISM: Homo sapiens

<400> SEQUENCE: 2
gagagagcga tagagagaga gagagagaca tgagaatgaa tatgaatccc agccagcaag      60
aaagaaaaga tacttaacta aagatgcagg gaagttttgc ctcttcctga aaattatatt     120
attagctttt taaaaatcag gatgactgct agttttgttt aaagtatttg ttctggaaat     180
actaaagttg gagtctacca gactgaggtt agaagcattt tctttggcag caagaagata     240
attttataga agccatgcct gttcttgggg ttgcctcaaa actgaggcag ccagctgttg     300
ggtcaaagcc tgtgcatact gctcttccga taccaaatct tggcactact gggtcacagc     360
actgttcttc aagacctttg gaacttactg aaacagagag ctccatgctt tcttgtcagc     420
ttgcgttaaa atcaacctgt gaatttggag agaagaaacc cctccaagga aaagccaagg     480
agaaagaaga cagcaagatt tacactgact gggccaacca ctacctagca aaatcaggcc     540
acaagcggct gatcaaggac ttgcaacaag acattgcaga tggagtactc ctagcagaaa     600
tcatccagat tattgcaaat gaaaaagttg aagatatcaa tggatgtcct agaagtcagt     660
ctcagatggt aagatgagaa gatgaggttc ttaaccaaat agggaagaga taaaatactg     720
gaatgctctt aaaggtttaa taaaatctta tatatggcat actgcaaaat tgtagcacta     780
tgactcagag gagt                                                       794

<210> SEQ ID NO 3
<211> LENGTH: 7340
<212> TYPE: DNA
<213> ORGANISM: Homo sapiens

<400> SEQUENCE: 3
gagagagcga tagagagaga gagagagaca tgagaatgaa tatgaatccc agccagcaag      60
aaagaaaaga tacttaacta aagatgcagg gaagttttgc ctcttcctga aaattatatt     120
attagctttt taaaaatcag gatgactgct agttttgttt aaagtatttg ttctggaaat     180
actaaagttg gagtctacca gactgaggtt agaagcattt tctttggcag caagaagata     240
attttataga agccatgcct gttcttgggg ttgcctcaaa actgaggcag ccagctgttg     300
ggtcaaagcc tgtgcatact gctcttccga taccaaatct tggcactact gggtcacagc     360
actgttcttc aagacctttg gaacttactg aaacagagag ctccatgctt tcttgtcagc     420
ttgcgttaaa atcaacctgt gaatttggag agaagaaacc cctccaagga aaagccaagg     480
agaaagaaga cagcaagatt tacactgact gggccaacca ctacctagca aaatcaggcc     540
acaagcggct gatcaaggac ttgcaacaag acattgcaga tggagtactc ctggcagaaa     600
tcatccagat tattgcaaat gaaaaagttg aagatatcaa tggatgtcct agaagtcagt     660
ctcagatgat tgaaaatgtt gatgtctgcc ttagttttct agcagccaga ggggtaaatg     720
ttcaaggtct atctgctgaa gaaataagaa atggaaactt aaaagccatt ctagggctgt     780
ttttcagttt atctcgctac aagcagcaac acaccatca acaacagtac tatcagtcct     840
tggtggaact tcagcagcga gttactcacg cttcccctcc atcggaagcc agccaggcca     900
```

```
aaacccagca agatatgcag tccagtctgg cagccagata tgcaactcag tctaatcaca    960
gtggaattgc aaccagtcaa aaaaagccta ctaggcttcc agggccctct agggtgcctg   1020
ctgcaggaag cagcagcaag gtccagggag cctctaattt aaataggaga agtcagagct   1080
ttaacagcat tgacaaaaac aagcctccaa attatgcaaa tggaaacgaa aaagattcct   1140
ccaaaggacc tcaatcgtct tcaggtgtaa atggtaacgt gcagcctccc agtactgctg   1200
ggcagcctcc tgcctctgcc atcccttctc caagtgccag caagccctgg cgcagcaagt   1260
ccatgaatgt caaacacagt gccacctcca ccatgttgac tgtaaagcag tcaagtacag   1320
ccacctcccc cacaccatct tcagacagac tgaagccacc tgtctcagaa ggggtcaaaa   1380
ctgctccctc aggacagaaa tccatgcttg agaaattcaa gctagtcaat gcccggactg   1440
ctttacgccc cccgcagcct cccagttcag gacctagtga tggtgggaag gatgatgatg   1500
ccttttctga atctggtgaa atggaaggtt ttaacagtgg tctgaatagt ggtggctcaa   1560
caaatagcag tcccaaagtg tcacctaagt tggcccctcc aaaagctgga agcaaaaatc   1620
tcagcaataa aaagtctttg ctacagccaa aggaaaaaga agaaaagaac agggacaaaa   1680
ataaagtttg cactgaaaaa ccagtcaaag aagagaagga tcaggtgaca gagatggctc   1740
caaaaaagac ctccaaaatt gcaagcttga tccctaaggg cagcaagaca acagcagcta   1800
agaaggaaag cttaattccg tcttccagtg gtattccaaa accaggctct aaagttccaa   1860
cagtaaagca aaccatttca cctggcagca cagcaagcaa agagtctgag aaattcagga   1920
ctaccaaggg gagcccttcc cagtccttat ctaagcctat aaccatggag aaagcaagtg   1980
cttctagttg tcctgcccct ttggaaggaa gggaagctgg ccaagcttct ccttctggtt   2040
cctgtaccat gacagtggca caaagcagtg ggcagagcac aggaaatggt gctgtccaac   2100
tccctcaaca gcagcaacat agccacccga ataccgcgac agtggcacca ttcatttaca   2160
gggcacattc agaaaatgaa ggtaccgctt taccatcggc tgactcctgt accagtccta   2220
caaagatgga cttatcatat agtaagactg ctaagcagtg cctggaggag atatctggtg   2280
aagaccctga acaagaaga atgagaacag ttaaaaacat agcagacttg aggcagaatt   2340
tagaagagac tatgtccagt cttcgtggga ctcagataag ccacagcacc ctggagacaa   2400
catttgacag cactgtgaca acagaagtta atggaaggac catacccaac ttgacaagtc   2460
gacccacccc catgacctgg aggttgggcc aggcatgtcc gcgacttcag gcgggagatg   2520
ctccctccct gggtgctggc tatcctcgca gtggtaccag tcgattcatc cacacagacc   2580
cctcgaggtt catgtatacc acgcctctcc gtcgagctgc tgtctctagg ctgggaaaca   2640
tgtcacagat tgacatgagt gagaaagcaa gcagtgacct ggacatgtct tctgaggtcg   2700
atgtgggtgg atatatgagt gatggtgata tccttgggaa aagtctcagg actgatgaca   2760
tcaacagtgg gtacatgaca gatggaggac ttaacctata tactagaagt ctgaaccgaa   2820
taccagacac agcaacttcc cgggacatca tccagagagg ggttcacgat gtgacagtgg   2880
atgcagacag ctgggatgac agcagttcag tgagcagtgg tctcagtgac acccttgata   2940
acatcagcac tgatgacctg aacaccacat cctctgtcag ctcttactcc aacatcaccg   3000
tccctctag gaagaatact caggtgagga cagattcaga gaaacgctcc accacagacg   3060
agacctggga tagtcctgag gaactgaaaa accagaagaa gattttgac agccatgggg   3120
atgctggtgg caagtggaag actgtgtcct ctggacttcc tgaagacccc gagaaggcag   3180
ggcagaaagc ttccctgtct gtttcacaga caggttcctg gaagagggc atgtctgccc   3240
aaggaggggc gccatctagg cagaaagctg gaacaagtgc actcaaaaca cccgggaaaa   3300
```

```
ccgatgatgc caaagcttct gagaaaggaa aagctcccct aaaaggatca tctctacaaa    3360
gatctccttc agatgcagga aaaagcagtg agatgaagg gaaaaagccc ccctcaggca    3420
ttggaagatc gactgccacc agctccttttg gctttaagaa accaagtgga gtagggtcat    3480
ctgccatgat caccagcagt ggagcaacca taacaagtgg ctctgcaaca ctgggtaaaa    3540
ttccaaaatc tgctgccatt ggcgggaagt caaatgcagg gagaaaaacc agtttggacg    3600
gttcacagaa tcaggatgat gttgtgctgc atgttagctc aaagactacc ctacaatatc    3660
gcagcttgcc ccgcccttca aaatccagca ccagtggcat tcctggccga ggaggccaca    3720
gatccagtac cagcagtatt gattccaacg tcagcagcaa gtctgctggg gccaccacct    3780
cgaaactgag agaaccaact aaaattgggt cagggcgctc gagtcctgtc accgtcaacc    3840
aaacagacaa ggaaaaggaa aaagtagcag tctcagattc agaaagtgtt tctttgtcag    3900
gttcccccaa atccagcccc acctctgcca gcgcctgtgg tgcacaaggt ctcaggcagc    3960
caggatccaa gtatccagat attgcctcac ccacatttcg aaggttgttt ggtgccaagg    4020
caggtggcaa atctgcctct gcacctaata ctgagggtgt gaaatcttcc tcagtaatgc    4080
ccagccctag taccacatta gcgcggcaag gcagtctgga gtcaccgtcg tccggtacgg    4140
gcagcatggg cagtgctggt gggctaagcg gcagcagcag ccctctcttc aataaaccct    4200
cagacttaac tacagatgtt ataagcttaa gtcactcgtt ggcctccagc ccagcatcgg    4260
ttcactcttt cacatcaggt ggtctcgtgt gggctgccaa tatgagcagt tcctctgcag    4320
gcagcaagga tactccgagc taccagtcca tgactagcct ccacacgagc tctgagtcca    4380
ttgacctccc cctcagccat catggctcct tgtctggact gaccacaggc actcacgagg    4440
tccagagcct gctcatgaga acgggtagtg tgagatctac tctctcagaa agcatgcagc    4500
ttgacagaaa tacactaccc aaaaagggac taagatatac cccatcatct cggcaggcca    4560
accaagaaga gggcaaagag tggttgcgtt ctcattctac tggagggctt caggacactg    4620
gcaaccagtc acctctggtt tccccttctg ccatgtcatc ttctgcagct ggaaaatacc    4680
acttttctaa cttggtgagc ccaacaaatt tgtctcagtt taaccttccc gggcccagca    4740
tgatgcgctc aaacagcatc ccagcccaag actcttcctt cgatctctat gatgactccc    4800
agctttgtgg gagtgccact tctctggagg aaagacctcg tgccatcagt cattcgggct    4860
cattcagaga cagcatggaa gaagttcatg gctcttcatt atcactggtg tccagcactt    4920
cttctctttta ctctacagct gaagaaaagg ctcattcaga gcaaatccat aaactgcgga    4980
gagagctggt tgcatcacaa gaaaaagttg ctaccctcac atctcagctt tcagcaaatg    5040
ctcaccttgt agcagctttt gaaaagagct tagggaatat gactggccga ttgcaaagtc    5100
taactatgac agcggaacaa aaggaatctg aacttataga actaagagaa accattgaaa    5160
tgctgaaggc tcagaattct gctgcccagg cggctattca gggagcactg aatggtccag    5220
accatcctcc caaagatctt cgcatcagaa gacagcattc ctctgaaagt gtttctagta    5280
tcaacagtgc cacaagccat tccagtattg cagtggtaa tgatgccgac tccaagaaga    5340
agaaaaagaa aaactgggtg aactctagag gaagtgagct gagaagttct ttcaaacaag    5400
cctttgggaa gaaaaagtcc accagcctcc cttcatcaca ttctgacatt gaagagctta    5460
ctgattcatc ccttccggca tcccccaagt taccccataa tgctggtgac tgtggctcag    5520
catccatgaa gccctcacaa tctgcttcag cgatctgtga atgcacagaa gctgaggcag    5580
agataattct gcagctgaag agcgagctca gagaaaagga attaaaatta acggatattc    5640
```

-continued

```
ggctggaggc cctcagctct gctcatcatc ttgatcagat ccgggaagcc atgaaccgga    5700
tgcagaatga aattgaaata ctgaaagctg aaaatgaccg gttgaaggca gaaactggta    5760
acacagctaa gcctactcgg ccaccgtcag aatcctcaag cagcacctcc tcttcatctt    5820
ccaggcagtc attaggactt tctctaaaca atttgaacat cacagaggct gttagctcag    5880
atattttgct agatgatgct ggtgatgcaa ctggacataa agatggccgc agtgtgaaaa    5940
ttatagtctc cataagcaag ggctatggtc gagcaaagga ccaaaaatct caggcatatt    6000
tgataggatc cattggtgtt agtggaaaaa ccaagtggga tgtcttagat ggtgtaataa    6060
gacgtctctt taaggaatat gtattccgaa ttgatacatc cactagcctt ggtctgagct    6120
ctgactgcat tgctagctac tgtataggag acttaattag atcccataac ctagaagtgc    6180
ctgaattgct gccttgtgga taccttgttg gagataataa catcatcact gtgaacctca    6240
aaggggtaga agaaaatagt ttggacagtt ttgtttttga tacgctgatt cctaaaccaa    6300
ttacccaaag gtactttaac ttgttgatgg agcatcacag aattatactc tcaggaccga    6360
gtggtactgg aaagacctat ttggcaaaca aacttgctga atatgtaata accaaatctg    6420
gaaggaaaaa aacagaggat gcaattgcca cttttaatgt ggaccacaag tcaagtaagg    6480
aattgcaaca atatctagct aacctggctg aacagtgcag tgctgataat aatggagtgg    6540
agctcccagt tgtaataatt cttgataatc ttcagggctc tctgagtgat atcttcaatg    6600
gttttctcaa ttgtaaatac aacaaatgtc catatattat tggaacaatg aatcagggag    6660
tttcttcatc accaaatcta gagctgcatc acaatttcag gtgggtatta tgtgcaaatc    6720
atacagaacc agtgaaaggc tttttaggca gatatcttcg aagaaaactc atagagatag    6780
aaattgaaag gaacattcgc aataatgacc tagtcaaaat tatagattgg attccgaaga    6840
cgtggcatca tctcaacagt tttttggaaa cacacagttc ttctgacgtt accattggtc    6900
cccgactatt ccttccttgc cccatggatg tagaaggttc tagagtatgg ttcatggatc    6960
tctggaacta ttctttagta ccttatattc tggaggcagt gagagagggt cttcagatgt    7020
atgggaaacg cacaccatgg gaagatcctt caaagtgggt gcttgacaca tatccatgga    7080
gctcagcaac tctgcctcag gagagcccag ccttacttca gctgcgacca gaagatgttg    7140
ggtatgaaag ctgcacatcc actaaggaag ccacaacctc aaagcacatt ccacaaactg    7200
acacagaagg agatcccctg atgaatatgc taatgaaact ccaagaagca gccaattact    7260
cgagcacaca aagctgcgac agcgaaagca ccagccacca tgaagacatt ttggattcat    7320
ctcttgaatc taccctctga                                                7340
```

METHOD FOR THE DIAGNOSIS OF LYMPHOPROLIFERATIVE DISEASES

This application is the US national phase of international application PCT/FI03/00061 filed 24 Jan. 2003, which designated the US and claims priority to FI Application No. 20020132 filed 24 Jan. 2002 and FI Application No. 20021617 filed 10 Sep. 2002. The entire contents of these applications are incorporated herein by reference.

FIELD OF THE INVENTION

The present invention relates to novel methods for the diagnosis and therapy of lymphoproliferative diseases. Specifically, the present invention relates to novel methods for the diagnosis and therapy taking advantage of the detection of chromosomal breakpoints in human chromosome 12 and/or translocation of chromosomal material from chromosome 12, said chromosomal breakpoints and/or translocation(s) being associated with lymphoproliferative diseases, such as primary cutaneous T-cell lymphomas (CTCL). The present invention further relates to the use of neuron navigator 3 gene (NAV3) or an equivalent or functional fragment thereof involved in chromosomal breakpoints in chromosome 12 and/or translocations thereof, said gene and/or translocations thereof being associated with lymphoproliferative diseases, such as primary cutaneous T-cell lymphomas (CTCL), as a diagnostic and therapeutic agent. The present invention also relates to the development of therapy.

BACKGROUND OF THE INVENTION

Primary cutaneous T-cell lymphomas (CTCL) represent a heterogeneous group of non-Hodgkin-lymphomas (NHL) whose etiology and pathomechanism are poorly understood [Siegel, R. S., et al., J. Clin. Oncol. 18 (2000) 2908-2925]. There is no curative therapy for CTCL. During the last ten years an increase of about 2-8% in the incidence of CTCL has been observed in the developed world [Doll, R., et al (Eds.), Trends in cancer incidence and mortality, cancer surveys, Vol 19/20, Cold Spring Harbor Laboratory Press, 1994, 423-53; Hjalgrim, H., et al., Br. J. Cancer 73 (1996) 951-54]. After the group of primary gastrointestinal lymphomas, CTCL together with the primary cutaneous B-cell lymphomas form the second most common group of extra-nodal NHL [Isaacson, P. G. and Norton, A. J., Cutaneous lymphoma, in Extranodal lymphomas, London, Churchill Livingstone, 1994, p. 172]. In Finland, a three-fold increase in the incidence of CTCL has been found in men, but not in women, during the last 40 years [Väkevä, L., et al., J. Invest. Dermatol. 115 (2000) 62-65].

A major portion, about 80%, of the CTCL patients usually show an indolent disease course and long remissions may be achieved with treatment. However, about 20% of the cases undergo a transformation into an aggressive large-cell variant so that the tumour cells invade several tissues, such as skin, blood, lymph nodes, and bone marrow, and there is some evidence that this is the original malignant cell clone [Wolfe, J., et al., J. Clin. Oncol. 13 (1995) 1751-57]. The 5-year survival of these patients is below 15% [Willemze, R., et al., Blood 90 (1997) 354-371; Siegel, R. S., et al., supra]. This transformation cannot be predicted by any current means.

The most common form of CTCL is mycosis fungoides (MF). The first skin lesions develop slowly. They resemble eczema or mild psoriasis and are called Parapsoriasis en plaques (Pps). In the early phases, poly- or oligoclonal CD4-positive lymphocytes infiltrate towards the epidermis of the skin. The time and the compartment of the malignant transformation are not known [Veelken, H., et al., J. Invest. Dermatol. 104 (1995) 889]. Malignant lymphocytes are later found also in blood and lymph nodes. However, recent data suggest that the malignant cells may be dispersed even earlier than previously thought [Karenko, L., et al., J. Invest. Dermatol. 108 (1997) 22-29; Karenko, L., et al., J. Invest. Dermatol. 112 (1999) 329-95: Karenko L, et al., J. Invest. Dermatol. 16 (2001) 188-193].

A more aggressive form of CTCL is the leukaemic Sezary syndrome (SS), which may evolve from MF or begin directly with erythrodermic skin symptoms.

In the treatment of CTCL, an early diagnosis is crucial, because the disease is prone to relapse in later stages. However, no means are available at present for a definite diagnosis of CTCL. In particular, MF is difficult to diagnose in its early presentations due to its resemblance to eczema or mild psoriasis and unfortunately may thus remain undetected in time. In the diagnosis of CTCL, a skin biopsy sample is obtained from the affected skin area and a histopathological analysis is performed. The histopathological diagnosis is based on the detection of epidermotropic, morphologically malignant lymphocytes, i.e. cells with hyperchromatic, indented (cerebrifom) nuclei (Willemze, R., et al., supra). In most, but not all, cases these cells express the CD4 surface marker, which may be detected immunohistochemically (Willemze, R., et al., supra). Thus, the diagnostic accuracy depends on visual grading and impression made by a pathologist, and early lesions with only very few malignant cells or with chromosomally clonal malignant lymphocytes with as yet normal morphology may be missed.

Additionally, the demonstration of T-cell receptor (TCR) rearrangement in blood or skin lesion-derived DNA has been used as a supplementary method in the diagnosis of CTCL. However, TCR rearrangement is not a disease-specific marker, since it identifies also reactive clonal cells [Guitart J. and Kaul K., Arch. Dermatol. 135 (1999) 158-62].

Also several chromosomal aberrations, especially numerical aberrations, have been observed in CTCL in molecular cytogenetic studies and these can be used in the diagnosis. In particular, the cytogenetic changes have been shown to precede the histologically identifiable malignancy [Whang-Peng, J., et al., Cancer 50 (1982) 1539; Berger, R., et al., Cancer Genet Cytogenet 27 (1987) 79; Karenko et al., 1997, supra]. However, in the early phases of the disease these abnormalities have been non-clonal, which renders the detection non-specific.

It is of highest importance to develop new methods, which enable an early diagnosis and the follow-up of therapeutic interventions in terms of residual malignant cells in lymphoproliferative diseases, such as CTCL. Also, additional means for the development of new guidelines for the initiation and follow-up of therapy are greatly needed.

SUMMARY OF THE INVENTION

We have now identified specific recurrent chromosomal breakpoints and/or translocations, which are associated with cutaneous T-cell lymphoma (CTCL), in chromosome 12, specifically in 12q14-12q24. We have also identified a gene involved in such chromosomal breakpoints and/or translocations. The identification of such specific chromosomal breakpoints and/or translocations and the gene and/or translocation, deletions or other defects of the gene allows the development of novel diagnostic and therapeutic methods for the detection and follow-up and treatment of lymphoproliferative diseases, such as CTCL.

The object of the invention is to provide novel methods and means for the diagnosis of lymphoproliferative diseases, such as CTCL, such methods and means allowing an early diagnosis of the disease.

Another object of the invention is to provide novel methods and means for the diagnosis of lymphoproliferative diseases, such as CTCL, such methods and means being specific and reliable.

Yet another object of the invention is to provide novel methods and means for the prediction of the progression of the disease and its transformation to an aggressive form in lymphoproliferative diseases, such as CTLC, such methods and means allowing a timely therapeutic intervention, which may be life-saving.

Still another object of the invention is to provide novel methods and means for the development of new guidelines for the initiation and follow-up of therapeutic interventions as well as for the development of new treatment modalities for lymphoproliferative diseases, such as CTCL, such methods and means prolonging the remission stage of the disease and introducing new possibilities for combating the disease and for the recovery of the patient.

The present invention relates to a novel method for the diagnosis and the follow-up of the lymphoproliferative diseases, such as CTCL, comprising the detection of the presence or the absence of at least one specific chromosomal breakpoint in chromosome 12 and/or at least one translocation of chromosomal material from chromosome 12, said chromosomal breakpoint and/or translocation being associated with said lymphoproliferative diseases, in a clinical sample.

The present invention further relates to a novel method for the diagnosis and the follow-up of the lymphoproliferative diseases, such as CTCL, comprising the detection of the presence or the absence of neuron navigator 3 (NAV3) gene or an equivalent or a functional fragment thereof associated with said lymphoproliferative diseases in a clinical sample.

The present invention still further relates to a novel method for the diagnosis and the follow-up of the lymphoproliferative diseases, such as CTCL, comprising the detection of the presence or the absence of a translocation or a deletion or another defect of neuron navigator 3 (NAV3) or an equivalent or fragment thereof in chromosome 12 associated with said lymphoproliferative diseases in a clinical sample.

The present invention also relates to rapid test systems for the identification of molecular cytogenetic alterations in clinical specimens obtained from patients suffering from a lymphoproliferative disease, such as CTCL, based on the detection of at least one specific chromosomal breakpoint in chromosome 12 and/or at least one translocation of chromosomal material from chromosome 12 and/or a translocation or a deletion or another defect of neuron navigator 3 (NAV3) gene or an equivalent or a functional fragment thereof in chromosome 12, said chromosomal breakpoint and/or translocation and/or gene translocation, deletion or defect being associated with the cytogenetic alterations.

The present invention further relates to a method of identifying patients who are in the risk of developing a lymphoproliferative disease, such as CTCL, or its leukaemic variant, and who could be helped by a timely therapeutic interaction by detecting the presence or absence of at least one specific chromosomal breakpoint in chromosome 12 and/or at least one translocation of chromosomal material from chromosome 12 and/or a translocation or a deletion or another defect of neuron navigator 3 (NAV3) gene or an equivalent or functional fragment thereof in chromosome 12, said chromosomal breakpoint and/or translocation and/or gene translocation, deletion or defect being associated with the disease subtypes in a biological sample obtained from said patients.

The present invention further relates to a method of predicting the progression of lymphoproliferative diseases, such as CTLC, and the transformation thereof to an aggressive variant by detecting the presence or absence of at least one specific chromosomal breakpoint in chromosome 12, specifically in 12q14-12q24, and/or at least one translocation of chromosomal material from chromosome 12 and/or a translocation or a deletion or another defect of neuron navigator 3 (NAV3) gene or an equivalent or a fragment thereof in chromosome 12, said chromosomal breakpoint and/or translocation and/or gene translocation, deletion or defect being associated with the disease subtypes, in a biological sample obtained from a patient suffering from said disease.

The present invention also relates to a use of a specific chromosomal breakpoint or specific chromosomal breakpoints in chromosome 12, specifically in 12q14-12q24, and/or a translocation of chromosomal material from chromosome 12, said chromosomal breakpoint and/or translocation being associated with lymphoproliferative diseases, such as CTCL, for the diagnosis of said diseases.

The present invention also relates to a use of neuron navigator 3 (NAV3) gene or an equivalent or a fragment thereof and/or of a translocation, a deletion or another defect of neuron navigator 3 (NAV3) gene or an equivalent or a fragment thereof in chromosome 12, said gene, translocation, deletion or defect being associated with lymphoproliferative diseases, such as CTCL, for the diagnosis of said diseases.

The present invention also relates to a use of a specific chromosomal breakpoint or chromosomal breakpoints in chromosome 12 and/or a translocation of chromosomal material from chromosome 12, said chromosomal breakpoint and translocation being associated with lymphoproliferative diseases, such as CTCL, for the development of therapy of said diseases.

The present invention also relates to a use of neuron navigator 3 (NAV3) gene or an equivalent or a fragment thereof and/or of a translocation, deletion or another defect of neuron navigator 3 (NAV3) gene an equivalent or a fragment thereof in chromosome 12 associated with lymphoproliferative diseases, such as CTCL, in therapy of said diseases.

BRIEF DESCRIPTION OF THE DRAWINGS

FIG. 3 shows a FISH analysis of a chromosome sample.

FIG. 3A). The uppermost sub-window shows a normal chromosome 12 (N1), which is also the middle chromosome in the group of three chromosomes 12 on the right-hand side of the background picture. The centromere of chromosome 12 is visible. YAC 803-C-2 is indicated in sub-windows and in the background pictures. BAC RP11-359M6 is visible in the uppermost sub-window and in the chromosome 12 in the middle in the group of chromosomes 12. The signal is missing in the two next sub-windows showing that it has moved away from the two other copies (T1 and T2) of chromosome 12. The signal is lacking also from the chromosomes on both sides of the normal chromosome 12 in the background picture, whereas the YAC 803-C-2 signal indicating presence of YAC 803-C-2 derived material is present in these two copies. The lowest sub-window depicts chromosome 18 (T3) that has received material corresponding to BAC RP11-359M6. The centromere of chromosome 18 is the upper signal and the lower signal is BAC. The corresponding chromosome 18 showing the translocated material is the leftmost (T3) chromosome 18 in the group of four chromosomes 18 in the background picture.

The exact breakpoint (question mark) within the limits of BAC RP11-494K17 is an approximation.

DETAILED DESCRIPTION OF THE INVENTION

The present invention is based on the identification of a specific breakpoint or specific breakpoints in chromosome 12q, specifically between 12q14-q24, with or without translocation of chromosomal material to other chromosomes, which breakpoints are associated with CTCL.

As used herein the terms "chromosomal breakpoint" and "chromosomal break" refer to a point from which the chromosome has lost material and is thus a structural abnormality of the chromosome. As used herein, the term "translocation" refers to transfer of chromosomal regions between non-homologous chromosomes.

As used herein the term "neuron navigator 3 gene" (NAV3) refers to the gene having the sequence identified as Seq. Id. Nr. 1 or an equivalent thereof having essentially the same function and encoding essentially the same protein, or that having the sequence identified as Seq. Id. Nr. 3 or an equivalent thereof. The term "equivalent" further includes functional fragments or variants of NAV3, such as the sequence identified as Seq. Id. 2, or a functionally equivalent isolated DNA sequences hybridizable thereto.

As used herein the term "functionally equivalent fragments" of NAV3 gene refer to such gene fragments, which are detectable in the methods of the invention.

As used herein the expression "deletion or another defect" of NAV3 gene refers to the absence of a nucleotide or nucleotides and/or an exon or exons in the gene sequence which absence adversely affects the function of the gene.

Figure 1:
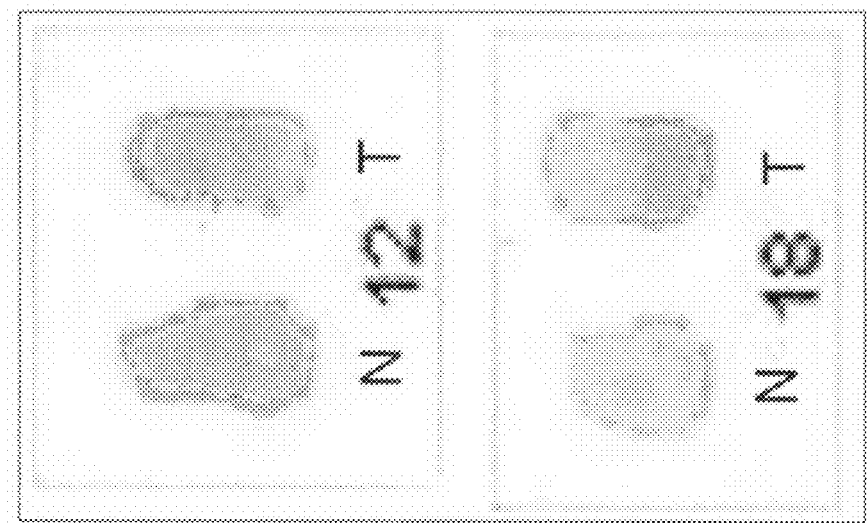
FIG. 1 shows a SKY analysis of a translocation between chromosomes 12q and chromosome 18q in a sample from a SS patient. Normal chromosomes are marked with N, translocated chromosomes with T.
Figure 2:
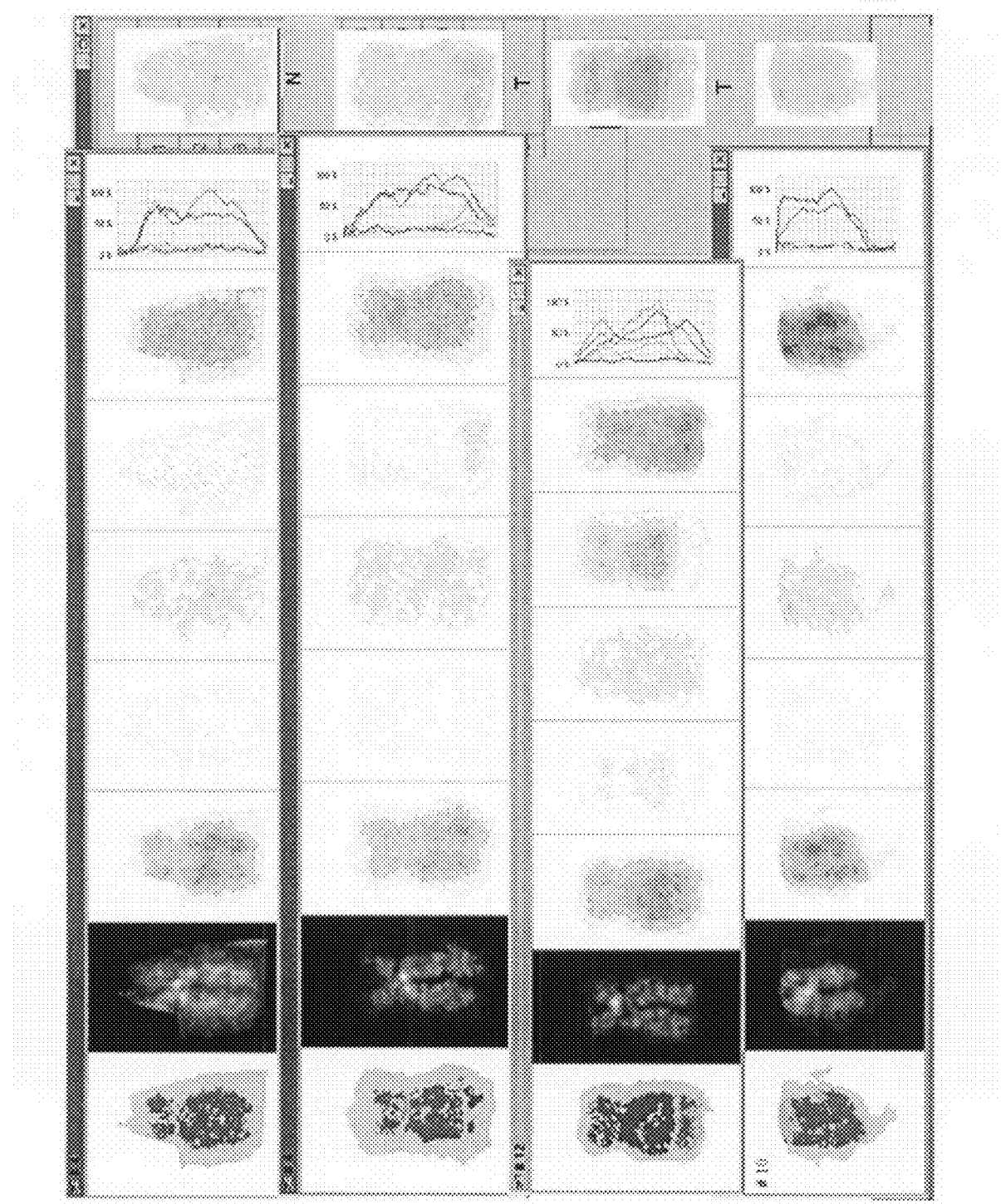
FIG. 2 shows a FISH-analysis of translocations between chromosomes 12q, 4q and 10. The uppermost sub-window shows a normal chromosome 4. The second sub-window shows a chromosome 4 with translocated material of chromosome 12 distally in the q-arm. The third sub-window shows chromosome 12q with a breakpoint in q22, and translocated material of chromosome 10 distally in the q-arm. The lowest sub-window shows chromosome 10. The combined colours of FISH of each chromosome are shown on the right-hand side of each sub-window (N=normal, T=translocation).
Figure 3A:
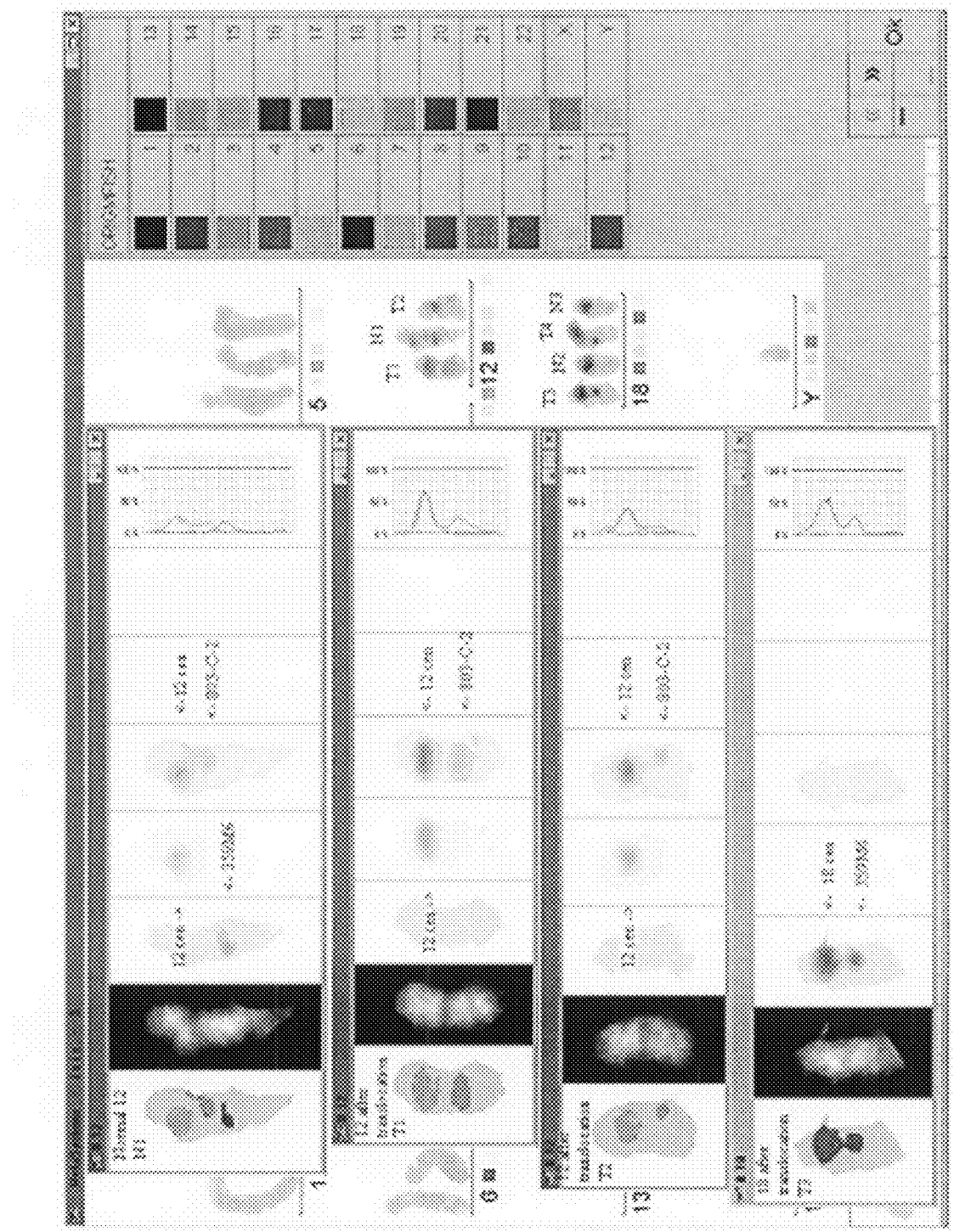
FIGS. 3A) and 3B) represent signal combinations of chromosomes 12 and 18 in the same cell. Combined signals of the chromosomes are seen on the right-hand side in both pictures. The signal spectra are seen in the middle sub-windows. The sample was obtained from the same patient as in FIG. 1.

A breakpoint was observed in the region 12q14-12q24 in 6 of 7 patients having Sezary syndrome (SS), the leukaemic form of CTCL, and in 3 of 4 patients with the Mycosis fungoides (MF; stage IA-IIB) subtype of CTCL (see FIGS. 1 and 2). In two patients, the breakpoint was specified to the region 12q14-q21.3 (FIG. 3). In one of these latter patients, the deletion in 12q was interstitial, so that the distal breakpoint was in 12q23 or 12q24. In 3 patients with SS the chromosome material was translocated to chromosome 18p or 18q12-18q21. In one SS patient translocation of chromosome 12 derived material occurred in chromosome 4 (FIG. 2) and a translocation to chromosome 22 was also observed.

The chromosomal breakpoints and translocations were identified with multicolour fluorescent in situ-hybridisation: either with combinatorial multi-fluor FISH [MFISH, Speicher, M. R., et al., Nat. Genet. 2 (1996) 368-375] or with spectral karyotyping [SKY; Schröck, E., et al., Science 273 (1966) 494-497]. The translocations and breakpoints were further specified with locus-specific commercial probes, YAC 803-C-2 (12q14-q15) and BAC RP11-359M6, with FISH. The Yac 803-C-2 is part of a published YAC-contig of 12q15 [Scoenmakers, et al., Genomics 29 (1995) 665-678]. It is located between DNA-markers STS 12-98 and STS-72, including those markers, and is situated near the proximal end of the contig. The Yac 803-C-2 is not chimeric. The YAC 803-C-2 contains high mobility group protein gene HMGI-C [Schoenmakers, et al., Nature Genetics 10 (1995) 436-444; Schoenmakers, et al., Genomics 29 (1995) 665-678]. The BAC RP11-359M6 is published [AC027288.26 8422 . . . 8574 in the www dot ncbi dot nlm dot nih dot gov (Roswell Park Cancer Institute Human BAC Library, complete sequence 177080]. The BAC RP11-359M6 contains the human PAWR-gene [localization 12q21; Johnstone, et al., Genomics 53 (1998) 241-243; for BAC, see www dot ncbi dot nlm dot nih dot gov]. The 12q24 is known to contain a retropseudogene HMGIY [Rogalla, et al., Cancer Genet. Cytogenet. 130 (2001) 51-56], which is another member of the high mobility group protein genes. In uterine leiomyomas, the mitochondrial aldehyde dehydrogenase (ALDH2) gene in 12q24.1 has been found a translocation partner to HMGIC [Kazmierczak, et al., Cancer Res 55 (1995) 6038-6039].

Figure 3B:
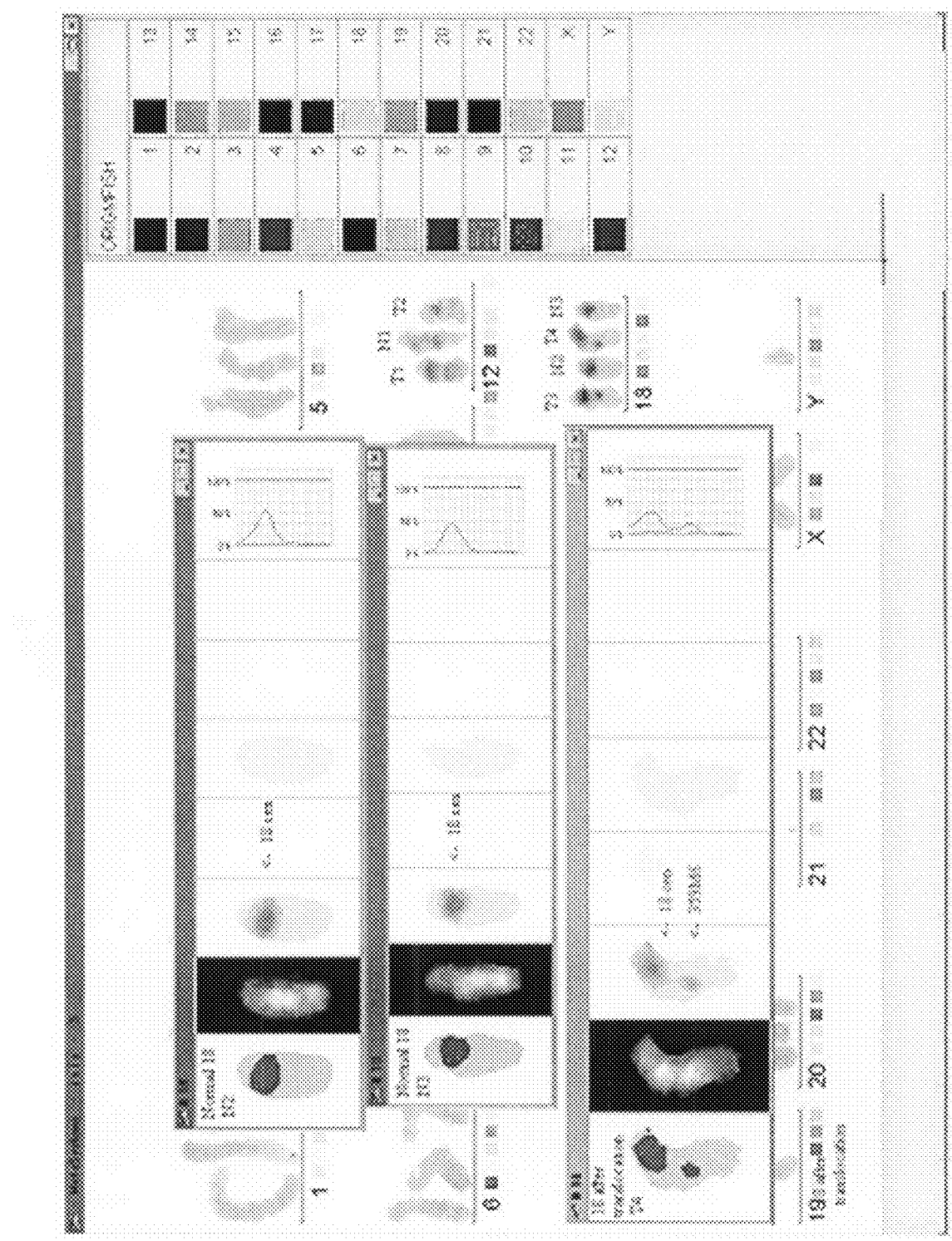
FIG. 3B). Two upper sub-windows represent normal chromosomes 18 (N2 and N3) showing only centromeres. The third sub-window shows chromosome 18 (T4) that has received material from chromosome 12 (the BAC 359M6 is the other signal under the centromere as indicated in FIG. 3B). This chromosome (T4) is the second from right in the background picture.

By a FISH analysis, the chromosomal breakpoint in 12q14-q21 and its translocation to 18q12-q21 in a biological sample obtained from an SS patient were observed as a disappearance of the green BAC RP11-359M6 spot from chromosome 12 (FIG. 3A, the uppermost sub-window, the normal chromosome, versus the two next sub-windows, defective chromosomes) and as an appearance of an additional green BAC RP11-359M6 spot in chromosome 18 (FIG. 3B, the two upper sub-windows, normal chromosomes, versus the lowest sub-window, the defective chromosome 18).

As a consequence of the chromosomal break and translocation, a tumour suppressor gene may be disrupted, or the transcription of a gene promoting cell growth or apoptosis may be amplified, or a neogene intervening with known transcription factors regulating cell growth may be formed inducing the transformation of the disease to its malignant form.

Figure 8:
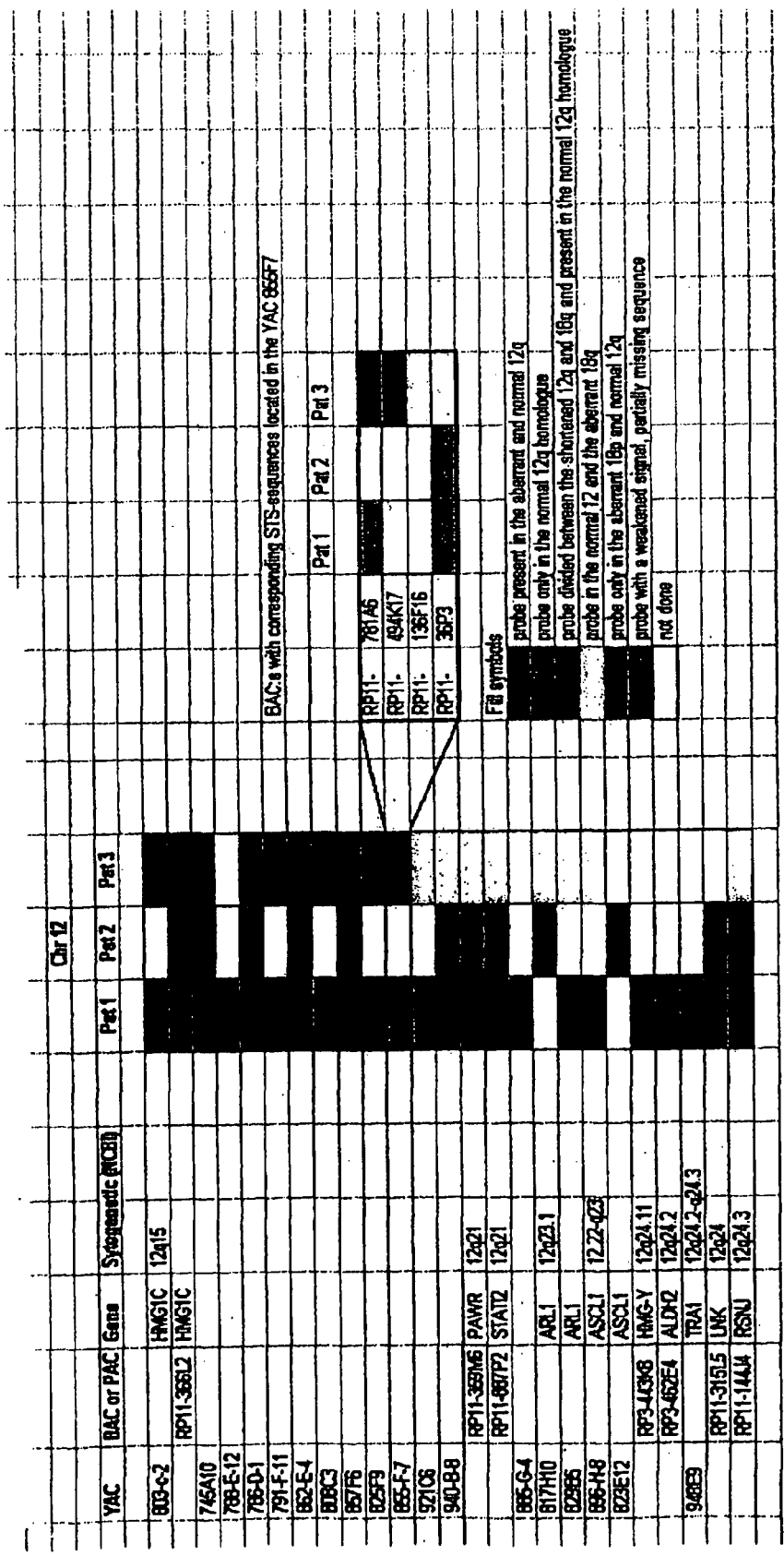
FIG. 8 shows the signals of YAC, BAC or Pac (P1) probes in a FISH assay with some corresponding genes in aberrant chromosome 12 observed in patients 1, 2 and 3 all suffering from SS, the leukaemic subtype of CTCL, demonstrating the long chromosomal distances studied with hybridisations

In order to further identify the breakpoints and translocations observed as well as to identify the translocated material further analyses with additional specific YAC- and BAC-probes were performed (FIG. 8).

Probe YAC 855F7 was seen to be divided between the aberrant chromosome 12 and the aberrant chromosome 18 showing that the translocation breakpoint in a patient sample studied was within the limits of this YAC. YAC 855F7 is part of the YAC-contig 12.4 (NIH: www dot ncbi dot nlm dot nih dot gov) and spans the region between markers CHLC.GATA65A12 and WI-6487. NCBI database revealed between those markers in the corresponding genomic contig (NT_009551) consecutive loci, i.e., LOC255379, LOC255315, LOC204040, LOC121318, and KIAA0938. According to PCR with locus-specific STS-markers and a BLASTA computer analysis (www dot ncbi dot nlm dot nih dot gov), these loci were found to be situated in YAC 855F7 DNA and four BACs: RP11-781A6, RP11-494K17, RP11-136F16, and RP11-36P3 (accession numbers AC073552.1, AC022268.5, AC073571.14, and AC073608.19, respectively).

The BAC RP11-494K17 contains locus 255315 and almost the whole locus 204040. A part of the latter locus is also present in BAC 136F16, which also contains the whole locus 121318 and a small part of KIAA0938. The BAC RP11-36P3 contains the whole locus KIAA0938, but not the sequence of locus 121318. The BAC 781A6 contains locus 255379 and a small part of locus 255315 (see FIG. 8)

According to the BLASTA-analysis and Maes et al. [Genomics 80 (2002) 21-30], loci 255315, 203040, 121318, and KIAA0938 together form a RAINB1-gene homologue, neuron navigator 3 (NAV3) gene (Seq. Id. Nr. 1) or a partial coding sequence thereof (AF397731). LOC 255315 (Seq. Id. Nr. 2) shares its sequences 498 to 668 with the NAV3 sequence 1 to 171 except for one nucleotide in position 594. A NAV3 gene sequence containing full 5' terminal is set forth as Seq. Id. Nr.3.

Figure 4:
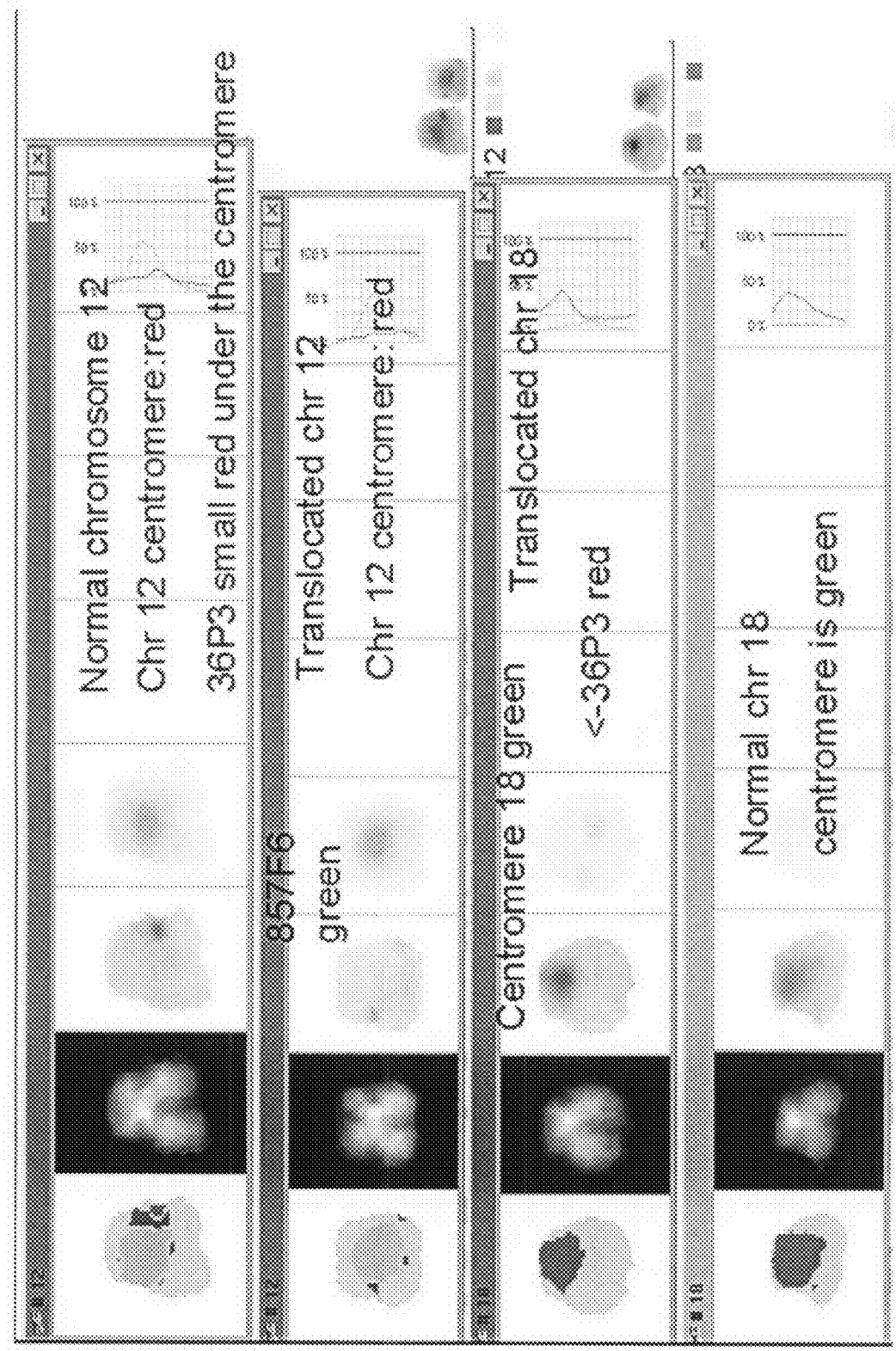
FIG. 4 shows a FISH-analysis of a translocation between chromosomes 12 and 18 using BAC 36P3 and YAC 857F6. The uppermost sub-window shows a normal chromosome 12: the centromere signal; a small BAC 36P3 signal under the centromere; and YAC 857F6 signal are indicated in FIG. 4. The second sub-window shows aberrant chromosome 12, from which chromosomal material has translocated to chromosome 18. The centromere signal is indicated in FIG. 4; BAC 36P3 is no more detected; YAC 857F6 is the-green signal indicated in FIG. 4. The third sub-window shows an aberrant chromosome 18: the centromere gives a signal as indicated in FIG. 4; BAC36P3 gives the signal indicating translocated material from chromosome 12. The lowest sub-window shows normal chromosome 18: the centromere gives the signal as indicated in the FIG. 4. The combined signals of FISH of each chromosome are shown on the right hand side of each sub-window. The upper background picture shows normal and aberrant chromosome 12 on the left hand and right hand side, respectively, and the lower background picture shows normal and aberrant chromosome 18 on the right-hand and left-hand side, respectively.

By a FISH analysis, the above-observed chromosomal breakpoint in 12q14-q21 and the translocation t(12;18)(q21;q12-21) in a biological sample obtained from an SS patient were confirmed by the disappearance of the red BAC 36P3 spot from chromosome 12 (FIG. 4A, the uppermost sub-window, the normal chromosome, versus the next sub-window, the aberrant chromosome) and by the appearance of an additional red BAC 36P3 spot in chromosome 18 (FIG. 4, the third and fourth sub-windows, aberrant chromosome 18 and normal chromosome 18, respectively). YAC 857F6 remained in chromosome 12. The translocation of chromosomal material from chromosome 12 to chromosome 18 was observed also by a SKY-analysis (FIG. 1).

Figure 5:
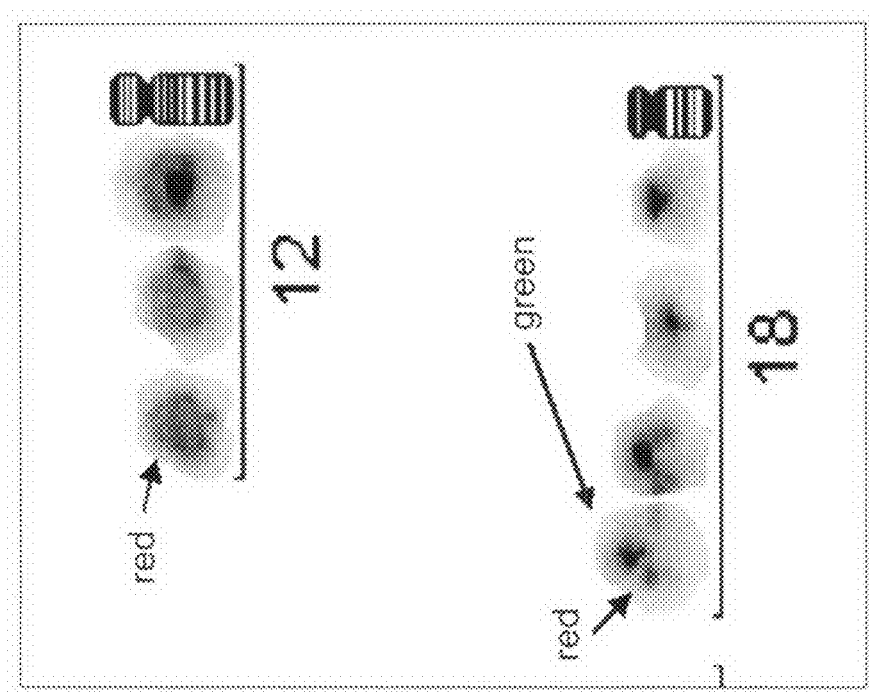
FIG. 5 shows a FISH-analysis of a translocation between chromosomes 12 (centromere signal indicated in FIG. 5) and 18q (centromere signal indicated in FIG. 5) with BAC 36P3 in a sample from a SS patient. The upper row from the left to the right: two aberrant chromosomes 12 and one normal chromosome 12; the centromere of chromosome 12 and BAC36P3 both give signals as indicated in FIG. 5, which are merged due to the shortness of chromosome 12. The lower row from left to the right: two aberrant chromosomes 18 and two normal chromosomes 18 with the centromere giving the signal as indicated in FIG. 5, and the translocated BAC 36P3 the signal indicated in FIG. 5.

A translocation between chromosomes 12 (centromere red) and 18q (centromere green) with BAC 36P3 in a sample from a SS patient was further confirmed by an additional FISH-analysis (FIG. 5)

Figure 6:
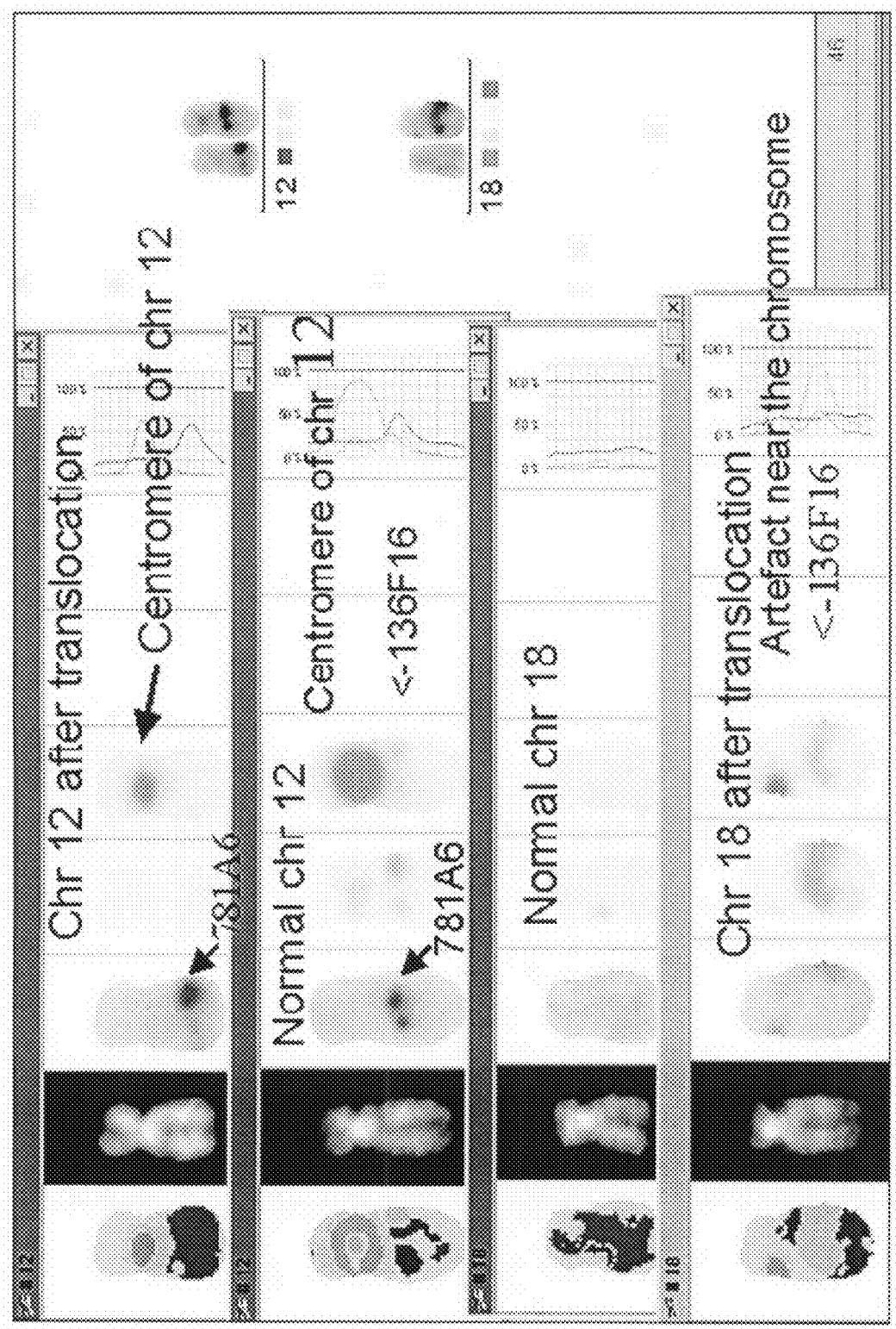
FIG. 6 shows a FISH-analysis of translocations between chromosomes 12 and 18 using BAC 781A6 (signal indicated in FIG. 6) and BAC 136F16 (signals indicated in FIG. 6). The uppermost sub-window shows chromosome 12 after translocation: the centromere signal is indicated in FIG. 6; BAC 136F16 is absent; BAC 781A6 gives a signal indicated in FIG. 6. The second sub-window shows a normal chromosome 12: the centromere signal is indicated in FIG. 6; BAC 136F16 gives the double signal indicated in FIG. 6 under the centromere; BAC 781A6 gives the signal indicated in FIG. 6. The third sub-window shows normal chromosome 18 without specific signals. The lowest sub-window shows chromosome 18 after translocation: BAC 136F16 gives double signal indicated in FIG. 6. The combined signals of FISH of each chromosome are shown on the right-hand side of each sub-window. The upper background picture shows normal and aberrant chromosome 12 on the right hand and left hand side, respectively, and the lower background picture shows normal and aberrant chromosome 18 on the left-hand and right-hand side, respectively.
Figure 7:
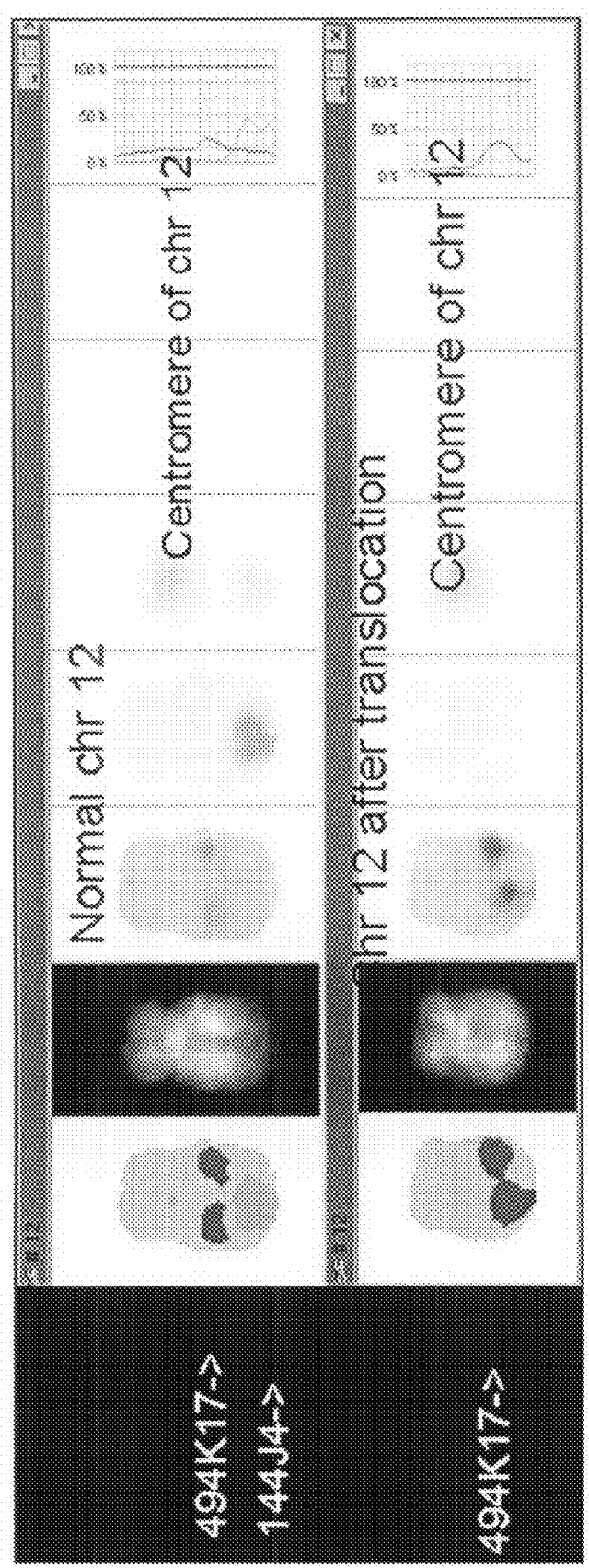
FIG. 7 shows a FISH-analysis of chromosome 12 using BAC494K17 (signal indicated in FIG. 7) and BAC 144J4 (12q24)(signal indicated in FIG. 7). The upper sub-window shows normal chromosome 12: the centromere gives a signal indicated in FIG. 7. The lower sub-window shows chromosome 12 after translocation: BAC 494K17 (signal indicated in FIG. 7) remains; BAC 144J4 has disappeared.

In a further FISH analysis with a SS patient sample, BAC 781A6 (a green signal in FIG. 6) and BAC136F16 (a red and a wine red signal in FIG. 6) separate from each other in the translocation as judged from the absence of the red spot and the presence of green spot in the aberrant chromosome 12 when compared to normal chromosome 12. This material has translocated to chromosome 18 (see red spot in the aberrant chromosome 18 in FIG. 6). On the other hand, BAC 494K17 remains in chromosome 12 (the green signal in aberrant chromosome 12 in FIG. 7) and BAC 144J4 moves away from chromosome 12 (a missing red signal in aberrant chromosome 12 in FIG. 7)

As the BACs above contain loci that together form the NAV3 gene, the separation of signals indicating the separation of loci shows the splitting up of the NAV3 gene to two parts in the translocation, one part remaining in chromosome 12 (the parts and loci situated in BACs RP11-786A1 and 494K17), the other part (the parts and loci situated in BACs 136F16 and 36P3) translocating to chromosome 18q.

The breakpoint deduced from by the FISH-experiments is situated in the distal part of the region covered by BAC 494K17 (possibly locus 204040, FIG. 8). More exact definition will require DNA-level studies, for example, cloning of the translocation breakpoint.

This is the first time that a specific recurrent breakpoint or translocation has been observed in CTCL, although other malignancies of the hematopoietic system with chromosomal break points/translocations have been described. The best known is the translocation between chromosomes 9 and 22, resulting in the so-called Philadelphia chromosome, which has been identified in CML [Nowell, P. and Hungerford, D., Science 132 (1960) 1497; Rowley, J., Nature 243 (1973) 290-293.]. This transformation results in the fusion of BCR and ABL genes, which is essential for the development of CML [Shtivelman, E., et al., Nature 315 (1985) 550-554]. The fusion gene has tyrosine kinase activity. The MLL (Mixed Lineage Leukemia) gene is a common target for chromosomal translocations associated with human acute leukemias. The latter translocations result in a gain of MLL function by generating novel chimeric proteins containing the amino-terminus of MLL fused in-frame with one of 30 distinct partner proteins. Expression of this fusion protein is necessary but not sufficient for leukemogenesis in the mouse model [Ayton, P. and Cleary, M., Oncogene 20 (2001) 5695-707].

Acute promyelocytic leukemia is characterized by t(15;17) translocation (Xu et al., Leukemia 9 (2001) 1358-68], splenic marginal zone B-cell lymphoma by t(11:14)(p11;q32) translocation [Cuneo, A., et al., Leukemia 15 (2001) 1262-7], follicular lymphomas have t(14;18)(q32;q21) which results in the juxtaposition of the promoter region of IGH gene with the coding region of the anti-apoptotic protein Bcl-2 on chromosome 18 [Fukuhara, S., et al., Cancer Res 39 (1979) 3119-3128, Tsujimoto, Y. et al., Science 266 (1984) 1097-1099]. A recurrent, reciprocal balanced translocation t(2;5)(p23;q35) has been found in CD30+ anaplastic large-cell lymphomas [Kadin, M. E. and Morris, S. W., Leuk Lymphoma 29 (1998) 249-56] and in up to 50% of CD30+ primary CTCL [Beylot-Barry, M. et al., Blood 91 (1998) 4668-76]. This translocation creates a novel fusion protein, which has transforming properties in vitro.

Similarly, this is the first time that a specific gene, NAV3, and translocations thereof have been associated with lymphoproliferative diseases, such as CTCL.

Neuron navigator 3 (NAV3) gene is a member of a recently identified human gene family, which shows homology to the unc-53, a cell guidance gene from *Caenorhabditis elegans* (Maes et al., supra). It also shares homologous sequences with human RAINB1 (retinoic acid inducible in neuroblastoma cells) a mammalian homologue of unc-53 [Merrill et al., PNAS 99 (2002) 3422-3427]. NAV3 consists of 39 exons and its expression, based on mRNA detection, is largely restricted to the brain tissue (Maes et al., 2002, supra), but no haematopoietic or lymphoid tissues have been examined until now. NAV3 was shown to produce transcripts encoding proteins of different lengths and it may be subject to tissue-specific alternative splicing. The sub-cellular localization of NAV3 is not known. The homologous protein UNC-53, based on predicted structure, has two polyproline-rich domains that may represent SH3-binding domains, a doublet of central coiled-coil regions (possibly interacting with other proteins) and a putative ATP/GTP-nucleotide binding site. It also contains two putative actin-binding domains [Stringham, E., et al., Development 129 (2002) 3367-3379).

Based on the current knowledge of the aforementioned homologous genes and proteins, we assume that NAV3, as set forth in Seq. Id. Nr. 1 or Nr. 3, exerts its function in signal transduction, and its absence (gene deletion) or disturbed or amplified function (as a consequence of translocation) provides a growth favour, possibly via regulating response to apoptosis, for the cells, which in turn is the prerequisite for malignancy.

Retinoids are known to exert therapeutic activity in CTCL [Zackheim, H. S., Dermatology 199 (1999) 102-105), and since the NAV3 gene is likely to be induced by all-trans retinoic acid like its aforementioned homologues, it is understandable that the deletion/translocation of NAV3 as shown herein provides resistance to such therapy in vivo (as was the case with all three patients studied in the experiments shown herein).

Additionally, the present invention identifies a new potential function for NAV3 gene by showing its involvement in a lymphoproliferative disease, namely CTCL and especially, its leukaemic form Sezary syndrome.

The present invention characterizes cytogenetic findings and identifies the T cell clones with specific cytogenetic aberrations. The identified cells are truly malignant by definition, and the demonstration of such cells in clinical tissue specimen indicates the presence of the disease.

The present invention identifies translocations and eventual neogene formation as well as specific gene deletions and translocations associated with a lymphoproliferative disease, namely CTCL and especially, its leukaemic form Sezary syndrome. By integrating the above knowledge, a pathophysiological scheme with model characters for other lymphoproliferative diseases, new diagnostic tools are provided.

According to the diagnostic method of the present invention, the presence or absence of a chromosomal breakpoint or breakpoints can be detected from a biological sample by any known detection method suitable for detecting the breakpoints and translocations. Such methods are easily recognized by those skilled in the art and include fluorescence in situ hybridisations, such as multi-colour fluorescence in situ hybridisations, that are based on chromosome-specific or arm-specific painting probes that paint chromosome 12 with a specific colour, spectrum, colour ratio or colour intensity or their combination. The painting probe can be used alone or combined with other painting probes detecting other chromosomes or chromosome arms as in multi-fluor in situ-hybridisation [MFISH, described by Speicher, M. R., et al., Nat Genet 12 (1996) 368-375], or in spectral karyotyping [SKY, described by Schröck, E., et al, Science 273 (1996) 494-497], or in Combined binary ratio labelling [COBRA, described by Tanke, H. J., et al., Eur J. Hum. Genet 7 (1999) 2-11] or in colour changing karyotyping [CCK, described by Henegariu, O., et al., Nat. Genet. 23 (1999) 263-4], or with centromere specific probes, or with locus-specific or band-specific probes for loci in the translocating regions. Even the conventional G-banding techniques can be used in cases were the coarse detection of the translocation is regarded as sufficient. Preferable methods are those suitable for use in clinical laboratories, such as MFISH and SKY.

According to one preferred embodiment of the present invention, which takes advantage of the identification of NAV3 gene in the lymphoproliferative diseases, the presence or absence of the NAV3 gene or an equivalent or a fragment thereof can be detected from a biological sample by any known detection method suitable for detecting a gene expression (or copy number), i.e. methods based on detecting the copy number of the gene (or DNA) and/or those based on detecting the gene expression products (mRNA or protein). Such methods are easily recognized by those skilled in the art and include in situ hybridisations, such as fluorescence in situ hybridisation (FISH), mRNA in situ hybridisation, Northern analysis, RT-PCR, Southern and Western analyses, immunohistochemistry, and other immunoassays, such as ELISA. Preferable methods are those suitable for use in routine clinical laboratories, such as FISH, RT-PCR methods and immunohistochemistry.

In therapy, restoration of the normal function of the NAV3 gene can be used. This may be reached by enhancing the expression of functionally homologous genes, by introducing an intact NAV3 gene or by using an altered form of the NAV3 gene or antisense oligonucleotide against the NAV3 in any technique presently available for gene therapy to prevent the progression of a proliferating disease. In particular, tumor cell growth may be slowed down or even stopped by such therapy. Such techniques include the ex vivo and in situ therapy methods, the former comprising transducing or transfecting an intact or altered NAV3 gene (or its functional domains) in a recombinant or peptide form or as antisense oligonucleotides or in a vector to the patient, and the latter comprising inserting the altered gene or oligonucleotide into a carrier, which is then introduced into the patient. Depending on the disease to be treated, a transient cure or a permanent cure may be achieved. Alternatively, monoclonal or humanized antibodies or peptides binding to the NAV3 protein or to the fusion gene generated as a result of the translocation, can be used to suppress the function of the altered NAV3 protein and thus tumor cell growth may be slowed down or even stopped. Antibodies against NAV3 could also be used to carry other agents, such as cytotoxic substances, to the cancer cells overexpressing the NAV3 gene. Such agents could then be used to kill specifically the cancer cells.

The present invention also allows the development of rapid test systems for the identified molecular cytogenetic alterations in clinical specimens. Such systems include two DNA probes, which span the chromosomal breakpoint(s) and are labelled with different colourigenic or fluorescent markers, and which hybridise to easily obtainable non-dividing skin or blood cells (interphase cells). In case the chromosomal breakpoint in the region between the probes is present in the sample, the visualized signals either visually depart from each other, disappear or merge. Probes useful in this embodiment of the invention are, for example, those based on YAC:s or BAC:s, P1s or cosmids containing human locus-specific sequences. See also Example 2. The probes may be further developed by different procedures, for example PCR for enrichment of the human insert of the YAC, and different labelling procedures.

One embodiment of the invention is a diagnostic kit, which comprises reagents necessary for the detection of NAV3 gene, gene products or fragments thereof. These reagents can include specific antibodies, preferably monoclonal antibodies, capable of identifying NAV3 or its gene products or fragments thereof, other antibodies, markers and standards that are needed for visualization or quantification as well as buffers, diluents, washing solutions and the like, commonly contained in a commercial reagent kit. Alternatively, the diagnostic kit of the present invention may comprise NAV3 gene product or its functional variant or fragment together with suitable reagents, such as those listed above, needed for the detection of the antibodies against the NAV3 protein.

In the method of the invention, the biological sample can be any suitable tissue sample, such as a biopsy from the skin or lymph node, a body fluid, such as whole blood, lymph, or cerebrospinal fluid sample. The biological sample can be, if necessary, pretreated in a suitable manner known to those skilled in the art.

The detection of chromosomal breakpoints in chromosome 12 and/or translocation thereof is valuable especially in early diagnosis and in predicting the progression/transformation of lymphoproliferative diseases, such as primary cutaneous T-cell lymphomas (CTCL), by a combined diagnostic approach. For instance in CTCL, the recurrent breakpoint(s) in chromosome 12 and/or translocation(s) thereof detected in accordance with the present invention for the first time identify the aggressive forms of CTCL and, importantly, at an early stage of the disease. However, combining the demonstration of this chromosomal translocation with those to be described later on will provide a basis for creation of a pattern of chromosomal aberrations associated with a specific clinical course of lymphoproliferative diseases. Also, to confirm the functional capacity of the lymphocytes affected, the invention described herein may be combined to the demonstration of the surface markers of the cells as previously described for the known centromere-specific chromosomal probes [Karenko, L. et al., J. Invest. Dermatol. 116 (2001) 188-193].

The present invention provides a more reliable, earlier and easier diagnosis of lymphoproliferative diseases, such as CTCL, and opens new possibilities in the therapy thereof.

The following examples are given for further illustration of the invention.

EXAMPLE 1

Identification of a Translocation in Chromosome 12 a) Cell Culture and Conventional Chromosome Preparations

Peripheral blood lymphocytes were isolated with Ficoll-Isopaque density centrifugation, washed with RPMI 1640 (Gibco BRL, Life Technologies) and cultured for 3 days in RPMI 1640, in the presence of 20% Fetal Bovine Serum (Gibco BRL), L-Glutamine (100× Liquid, used as 1×, Gibco BRL), antibiotics (Penicillin 10 000 IU/ml, Streptomycin 10 000 micrograms/ml, used as 1:100), and Phytohemagglutinin (PHA 10576-015, Gibco BRL, used as 1:100). After this the cells were treated with hypotonic KCl-solution, fixed with glacial acetic acid-methanol (1:3) and the cell suspension was dropped on objective slides to make conventional chromosome preparations.

b) MFISH-Method

The air-dried preparations were fixed with 0.1% paraformaldehyde and dried in ethanol series (70%, 85%, 100%). A probe mixture containing painting probes specific for each chromosome pair labelled with a chromosome-specific fluorochrome combination (24XCyte-MetaSystems' 24 color kit, MetaSystems GmbH, Altlussheim, Germany) was denatured in a 75° C. water bath for 6 minutes, put briefly on ice, and kept 30 to 60 minutes in a 37° C. incubator according to the manufacturer's instructions. The DNA of the chromosomes was denaturated in 70% formamide in 2×SSC, pH 7.0, for 2 minutes, the slides were dried in 70%, 85% and 100% ethanol, respectively, and put on a 37° C. warm plate. The probe was applied on the chromosomes on the slides, and a cover slip was sealed with rubber cement (Starkey Chemical CO, IL, USA). The slides were incubated for 3 to 5 days in a moist chamber at 37° C.

The slides were washed with 50% formamide in 2×SSC, pH 7.3, at 42° C. for 2×5 minutes, then in 2×SSC, pH 7.0 at 42° C. for 2×5 minutes, and 4×SSC with 0.01% Tween 20 (=SSCT), pH 7.0, for 1 minute. The biotin labels were detected with one or two layers of streptavidin-Cy5 according to the manufacturer's instructions (B-tect kit, MetaSystems GmbH), and the preparations were mounted in antifade and DAPI (B-tect kit, Metasystems GmbH).

The metaphases were photographed with UV-microscope (Axioplan imagining 2, Zeiss, Germany) and analysed using the computer program Isis of MetaSystems GmbH with MFISH-program module.

The breakpoints were further defined with a conventional G-banding (Verma, R. S. and Babu, A., Human Chromosomes. Manual of basic techniques, 1st ed. Pergamon Press, New York, 1989), in which it was possible to find these translocated chromosomes among the marker chromosomes and deleted chromosomes.

1c) SKY-Method (Alternative to MFISH)

The SKY [described by Schröck, E., et al., Science 273 (1996) 494-497] was performed as recommended by ASI (Applied Spectral Imaging). Briefly, a probe mixture (from the SKY kit, ASI) was denatured and incubated at 37° C. for one hour. The slides were denatured in 70% formamide/2× SSC, and dehydrated. The probe was applied onto the metaphase spreads, and hybridised at 37° C. for two days. The biotinylated probe was detected with avidin-Cy5, and the digoxigenin labelled probe with mouse anti-digoxigenin antibodies followed by a goat anti-mouse antibody conjugated to Cy5.5.

Either with MFISH or SKY, a breakpoint was observed in the region 12q14-12q24 in 5 of 6 patients having Sezary syndrome (SS), the leukaemic form of CTCL, and in 2 patients with the Mycosis fungoides (MF) subtype of CTCL (FIGS. 1 and 2). In 3 patients with SS the chromosome material was translocated to chromosome 18p or 18q12-q21 (FIG. 3) and in one patient to chromosome 4 (FIG. 2).

EXAMPLE 2

Characterization of the Translocation

The translocation was further defined with FISH by using locus-specific YAC-probes or BAC-probes (YAC-probes, YAC from CEPH, Fondation Jean Dausset, France; BAC-probes from Research Genetics, Groningen, tThe Netherlands). The YACs were grown in AHC broth and purified according to the instructions of Genomesystems (St. Louis, Mo., USA). The BACs were grown and purified according the instructions of Research Genetics (Groningen). Both YACs and BACs were labelled with FITC (Fluorescein-12-dUTP, NEN Life Science Products, Inc, Boston, Mass., USA), Alexa 488® or Alexa 594® (both Molecular probes, Leiden, The Netherlands) or biotin (Oncor Inc. Gaithersburg, Md., USA) using nick translation. The BACs were grown and purified according the instructions of Research Genetics (Groningen). For the YAC 803-C-2 and BAC RP11-359M6, see the chapter "Detailed description of the invention".

The chromosomes involved were identified with centromere-specific probes of chromosomes 12 and 18, labelled with biotin, (Oncor Inc. Gaithersburg, Md., USA) or with digoxigenin (Oncor Inc). The biotin label was detected with two layers of avidin Cy3 (ExtrAvidin-Cy3 conjugate, Sigma-Aldrich, Saint Louis, Mo., USA) and biotinylated anti-avidin antibodies (goat, Vector) between them. The digoxigenin label was detected with anti-digoxigenin antibodies made in sheep (Roche, Mannheim, Germany) followed by anti-sheep antibodies made in donkey and labelled with FITC (Jackson West Grove, Pa., USA). The preparations were mounted with Vectashield® with DAPI (Vector Laboratories, Inc, Burlingame, Calif., USA).

The metaphases were photographed with UV-microscope (Axioplan imagining 2, Zeiss, Germany) and analysed using the computer program Isis of MetaSystems GmbH with MFISH-program module.

With the method above, the breakpoint was specified to the region 12q14-q21.3 in two patients (FIG. 3).

EXAMPLE 3

Identification of NAV3 Gene in the Translocation

For further identification of the translocation additional probes were used in FISH. YAC 855F7 (CEPH) was grown and purified and labelled with digoxigenin-11-dUTP (Roche) with nick-translation as described in Example 2. The hybridisation was performed as described above in Example 2 above and the hybridised probe was detected with sheep anti-digoxigenin-rhodamine antibodies (Roche, Mannheim).

The hybridised probe was photographed and analysed with ultraviolet microscope and Isis 3-computer program (FIG. 8). In the sample from patient 3 suffering from SS, the YAC 855F7 divided between two chromosomes, 12q and 18q. In other hybridisations with further YACs the YACs situated in regions above YAC 855F7 (see FIG. 8, patient response block) remained on their respective places in the aberrant 12q, and the YACs below YAC 855F7 were found to be translocated from the aberrant 12q to the aberrant chromosome 18q. In samples from patients 1 and 2, the YAC 855F7 was present only in the normal homologue of chromosome 12, and not visible in any other chromosome. Only one homologue of the genes represented in the YAC855F7, like NAV3, was present in the cells.

YAC 855F7, which is a part of the YAC-contig 12.4 (NIH: www dot ncbi dot nlm dot nih dot gov), spans the region between markers CHLC.GATA65A12 and WI-6487. Five consecutive loci, namely LOC255379, LOC255315, LOC204040, LOC121318, and KIAA0938 were found from NCBI database (www dot ncbi dot nlm dot nih dot gov) in the corresponding genomic contig (NT_009551). According to PCR of locus and BAC-specific STS-markers (SHGC-155034, G62498, SHGC-79622, and WI-6487, respectively) and BLASTA computer analysis (www dot ncbi dot nlm dot nih dot gov), these loci were found to be situated in YAC 855F7 DNA and in four BACs RP11-781A6, RP11-494K17, RP11-136F16, and RP11-36P3 (accession numbers AC073552.1, AC022268.5, AC073571.14, and AC073608.19, respectively).

The four BACs, RP11-781A6, RP11-494K17, RP11-136F16, and RP11-36P3, were purified, labelled, hybridised and photographed as described above. In the sample from patient 3 suffering from SS, the BAC RP11-781A6 and the BAC RP11-494K17 remained on their places in the aberrant chromosome 12, whereas BAC RP11-136F6 and BAC RP11-36P3 were translocated to chromosome 18q. In samples from SS-patients 1 and 2, one homologue corresponding to the BAC RP11-36P3 was totally absent the signal being present only in the normal 12q (FIG. 8, enlargement).

According to the BLASTA-analysis and Maes et al (2002), the above loci 255315, 204040, 121318 and KIAA0938 together form a RAINB1-gene homologue neuron navigator 3 (NAV3). This gene has Seq. Id. Nr.1 (AF397731) or alternatively 3.

Figure 9:
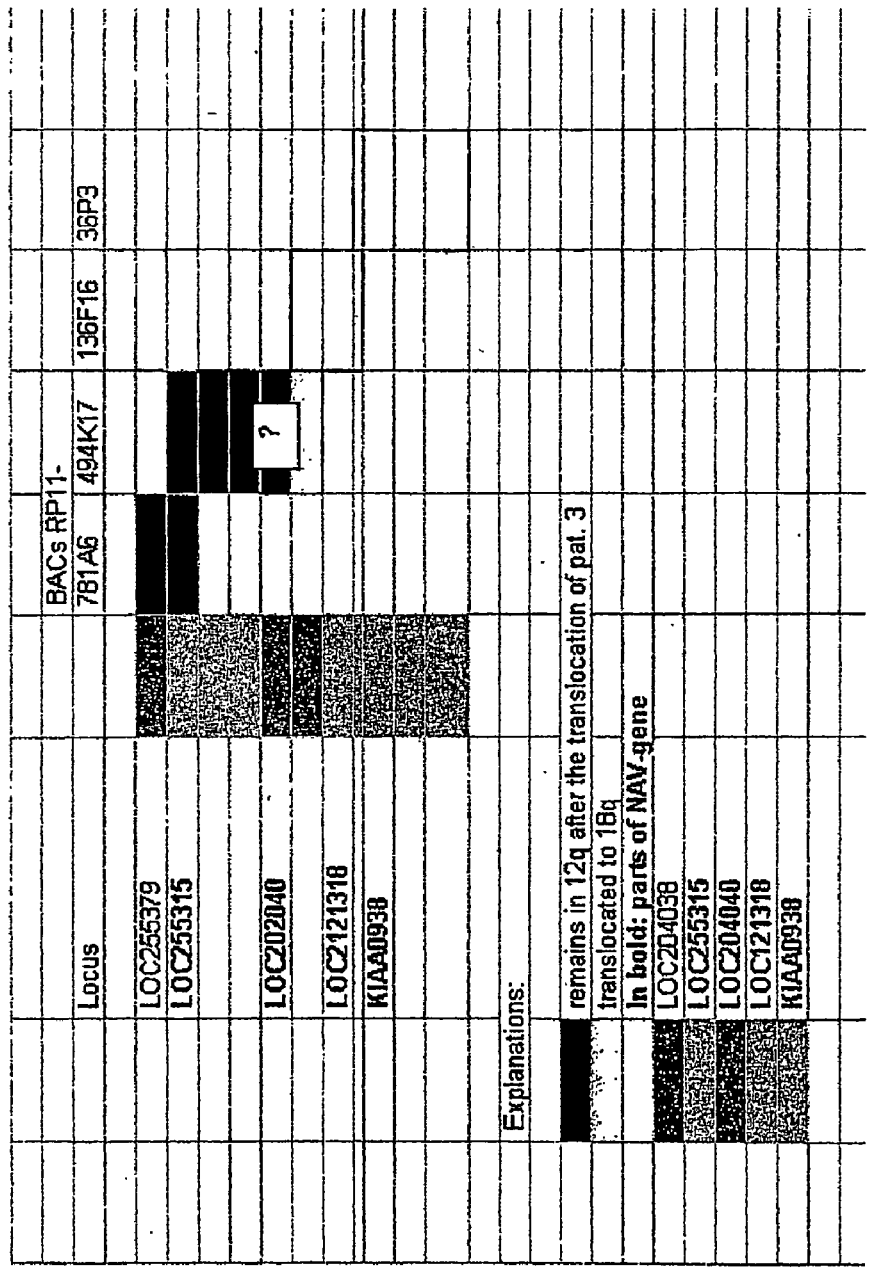
FIG. 9 shows the parts of the NAV3 gene involved in translocation in patient 3 as detected with FISH performed using BAC probes.

The BAC RP11-494K17 contains locus 255315 and almost the whole locus 204040. Part of the latter locus is also represented in BAC 136F16, as well as the whole locus 121318 and a small part of KIAA0938. The BAC RP11-36P3 contains the whole locus KIAA0938, but not sequence of locus 121318. The BAC 781A6 contains locus 255379 and a small part of locus 255315 (FIG. 9). Thus, in the translocation in the sample of patient 3, the NAV3 gene is split into two parts so that the other part remains in chromosome 12q but the other part translocates to chromosome 18q. In the samples from two other SS-patients studied, at least the lowest part of the gene (BAC RP11-36P3) is totally deleted.

The invention claimed is:

1. A method for diagnosis of Sezary syndrome (SS) by detecting the presence or absence of the neuron navigator 3 (NAV3) gene in a human patient, the method comprising:
i) analyzing a nucleic acid sample from a human patient to detect the presence or absence of a neuron navigator 3 (NAV3) gene having SEQ ID. NO: 1, said absence of the NAV3 gene being associated with said SS;
ii) identifying a human patient with said absence of the NAV3 gene, wherein the absence of the NAV3 gene is indicative of a deletion of the NAV3 gene; and
iii) diagnosing SS in said human patient based on the detection of said absence of the NAV3 gene.

2. A method for diagnosis of Sezary syndrome (SS) by detecting a deletion of the neuron navigator 3 (NAV3) gene in a human patient, the method comprising:
i) a analyzing a nucleic acid sample from a human patient to detect the presence or absence of a deletion of a neuron navigator 3 (NAV) gene having SEQ ID NO: 1, said deletion being associated with said SS;
ii) identifying a human patient with said deletion of the NAV3 gene; and
iii) diagnosing SS in said human patient based on the detection of said deletion of the NAV3 gene.

3. A method of claim 1, wherein the absence of NAV3 gene having SEQ ID. NO: 1 is detected in chromosome 12 in the region 12q14-12q24.

4. A method of claim 2, wherein the deletion of NAV3 gene having SEQ ID. NO: 1 is detected in chromosome 12 in the region 12q14-12q24.

5. A method of claim 1, wherein the nucleic acid sample is a metaphase spread.

6. A method of claim 2, wherein the nucleic acid sample is a metaphase spread.

* * * * *